(12) United States Patent
Efcavitch et al.

(10) Patent No.: US 10,059,929 B2
(45) Date of Patent: Aug. 28, 2018

(54) MODIFIED TEMPLATE-INDEPENDENT ENZYMES FOR POLYDEOXYNUCLEOTIDE SYNTHESIS

(71) Applicant: Molecular Assemblies, Inc., San Diego, CA (US)

(72) Inventors: J. William Efcavitch, San Carlos, CA (US); Juliesta E. Sylvester, La Jolla, CA (US)

(73) Assignee: Molecular Assemblies, Inc., San Diego, CA (US)

( * ) Notice: Subject to any disclaimer, the term of this patent is extended or adjusted under 35 U.S.C. 154(b) by 148 days.

(21) Appl. No.: 14/918,212

(22) Filed: Oct. 20, 2015

(65) Prior Publication Data

US 2016/0108382 A1 Apr. 21, 2016

Related U.S. Application Data

(60) Provisional application No. 62/065,976, filed on Oct. 20, 2014.

(51) Int. Cl.
| | | |
|---|---|---|
| *C12N 9/10* | (2006.01) | |
| *C12N 9/12* | (2006.01) | |
| *C12P 19/34* | (2006.01) | |

(52) U.S. Cl.
CPC ............ *C12N 9/1264* (2013.01); *C12P 19/34* (2013.01); *C12Y 207/07031* (2013.01)

(58) Field of Classification Search
None
See application file for complete search history.

(56) References Cited

U.S. PATENT DOCUMENTS

| | | |
|---|---|---|
| 8,808,989 B1 | 8/2014 | Efcavitch et al. |
| 2004/0043396 A1 | 3/2004 | Mueller et al. |
| 2011/0081647 A1 | 4/2011 | Siddiqi et al. |
| 2012/0202196 A1 | 8/2012 | Balasubramanian et al. |
| 2014/0141414 A1 | 5/2014 | Liu et al. |

OTHER PUBLICATIONS

Morrison and Weiss, "Combinatorial alanine scanning", (Current Opinion in Chemical Biology 5: 302-307 (2001).*
Delarue et al. "Crystal Structures of a Template-Independent DNA Polymerase: Murine Terminal Deoxynucleotidyltransferase," EMBO J. Feb. 1, 2002 (Feb. 1, 2002), vol. 21, pp. 427-439 (13 Pages).
International Serach Report and Written Opinion of the International Searching Authority dated Feb. 9, 2016 for International Application No. PCT/US2015/056467 (13 Pages).
Yang et al. "Mutational Analysis of Residues in the Nucleotide Binding Domain of Human Terminal Deoxynucleotidyl Transerase," J Biol Chem. Apr. 22, 1994 (Apr. 22, 1994), vol. 269, pp. 11859118-1185968 (10 Pages).

* cited by examiner

*Primary Examiner* — Anand U Desai
(74) *Attorney, Agent, or Firm* — Brown Rudnick LLP; Thomas C. Meyers

(57) ABSTRACT

The invention includes methods for identifying polymerases, such as modified terminal nucleotidyl transferases (TdT), that are capable of binding nucleotides comprising removable 3'-O-blocking moieties to a nucleic acid initiator, without the use of a template. The invention further includes the identified polymerases, and methods of using the polymerases for de novo synthesis of predetermined oligonucleotide sequences.

19 Claims, 10 Drawing Sheets

Specification includes a Sequence Listing.

MODIFIED TEMPLATE-INDEPENDENT ENZYMES FOR POLYDEOXYNUCLEOTIDE SYNTHESIS

RELATED APPLICATIONS

This Application claims priority to U.S. Provisional Application No. 62/065,976, filed Oct. 20, 2014, which is incorporated by reference in its entirety.

FIELD OF THE INVENTION

The invention relates to modified enzymes for de novo synthesis of polynucleotides with a desired sequence, and without the use of a template. As such, the invention provides the capability to make libraries of polynucleotides of varying sequence and varying length for research, genetic engineering, and gene therapy.

BACKGROUND

Most de novo nucleic acid sequences are synthesized using solid phase phosphoramidite-techniques developed more than 30 years ago. The technique involves the sequential de-protection and synthesis of sequences built from phosphoramidite reagents corresponding to natural (or non-natural) nucleic acid bases. Phosphoramidite nucleic acid synthesis is length-limited, however, in that nucleic acids greater than 200 base pairs (bp) in length experience high rates of breakage and side reactions. Additionally, phosphoramidite synthesis produces toxic by-products, and the disposal of this waste limits the availability of nucleic acid synthesizers, and increases the costs of contract oligo production. (It is estimated that the annual demand for oligonucleotide synthesis is responsible for greater than 300,000 gallons of hazardous chemical waste, including acetonitrile, trichloroacetic acid, toluene, tetrahydrofuran, and pyridine. See LeProust et al., *Nucleic Acids Res.*, vol. 38(8), p. 2522-2540, (2010), incorporated by reference herein in its entirety). Thus, there is a need for more efficient and cost-effective methods for oligonucleotide synthesis.

SUMMARY

The invention discloses modified terminal deoxynucleotidyl transferase (TdT) enzymes that can be used for de novo sequencing of oligonucleotides in the absence of a template. Methods for creating a template-independent polymerase through a combination of computational guidance and saturation mutagenesis, with a subsequent screen to identify functional mutants, are also disclosed. In some embodiments, the modified TdTs will include a mutation in the GGFRR or TGSR motifs, which interact with the nucleotide during synthesis.

Using the resulting enzymes, it will possible to synthesize de novo polynucleotides faster and cheaper. As such, the invention dramatically reduces the overall cost of synthesizing custom nucleic acids. In particular, the methods can be used to create template-independent transferases that can synthesize custom oligos in a stepwise fashion using modified 3' hydroxyl-blocked nucleotides. Because of the terminating group, synthesis pauses with the addition of each new base, whereupon the terminating group is cleaved, leaving a polynucleotide that is essentially identical to a naturally occurring nucleotide (i.e., is recognized by the enzyme as a substrate for further nucleotide incorporation).

The methods and enzymes of the invention represent an important step forward in synthetic biology because the enzymes will allow for aqueous phase, template-independent oligonucleotide synthesis. Such methods represent an improvement over the prior art in that they will greatly reduce the chemical waste produced during oligonucleotide synthesis while allowing for the production of longer polynucleotides. Furthermore, because the methods replace a chemical process with a biological one, costs will be reduced, and the complexity of automated synthetic systems will also be reduced. In an embodiment, a simple five-reagent delivery system can be used to build oligonucleotides in a stepwise fashion, and will enable recycling of unused reagents.

DESCRIPTION OF THE INVENTION

The invention facilitates the synthesis of polynucleotides, such as DNA, by providing modified enzymes that can be used with nucleic acid analogs. Using the disclosed methods, a modified template-independent terminal deoxynucleotidyl transferase (TdT) is obtained that allows the enzymatically mediated synthesis of de novo oligodeoxynucleotides, thereby enabling their use in routine assembly for gene synthesis. The enzymes of the invention lend themselves to aqueous-based, enzyme-mediated methods of synthesizing polynucleotides of a predetermined sequence on a solid support.

Figure 2:
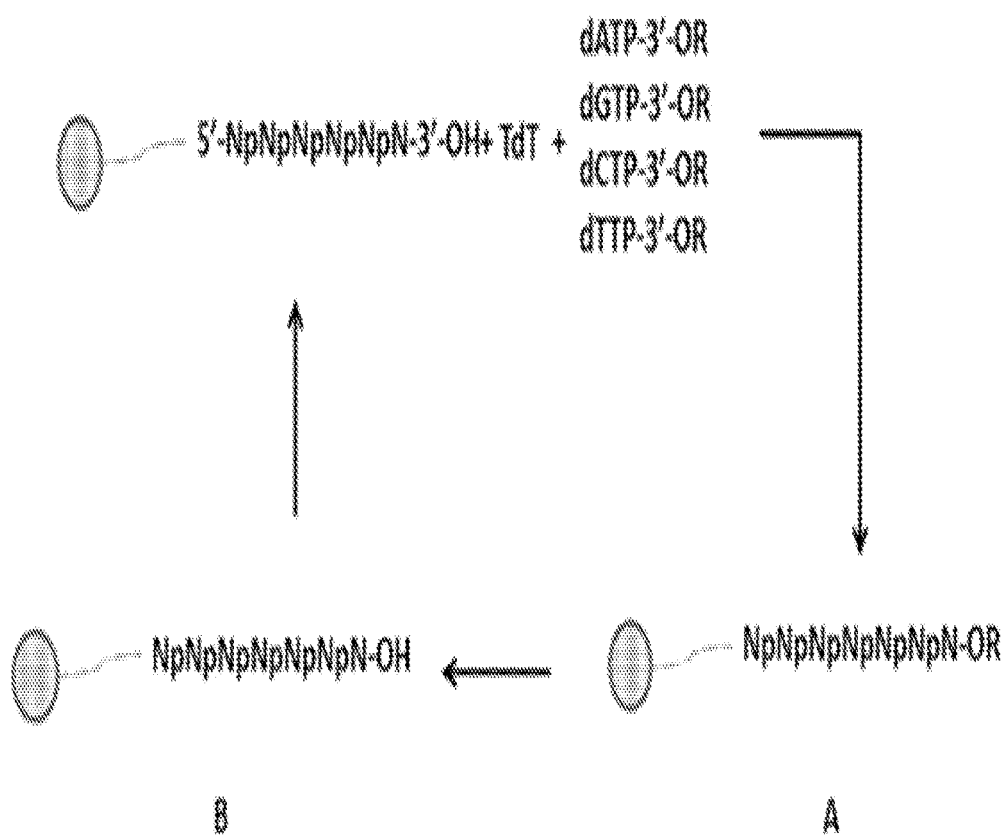
FIG. 2 illustrates an exemplary modified terminal deoxynucleotidyl transferase (TdT) mediated polynucleotide synthesis cycle using a support bound initiator and 3'-O-blocked nucleotide triphosphate including (A) incorporation of a nucleotide analog comprising a cleavable 3'-O-blocking group (indicated by R), and (B) removal of the 3'-O-blocking group thus enabling the next 3'-O-blocked nucleotide analog to be incorporated, wherein N=A, G, C, or T.

The modified enzymes of the invention will allow 3'-O-blocked dNTP analogs to be used in a step-by-step method to extend an initiating nucleic acid into a user defined sequence (see FIG. 2). Furthermore, after each nucleotide extension step, the reactants can be recovered and recycled from the solid support back to the original reagent reservoir. Once that step is complete, the 3'-O-blocking group will be removed, allowing the cycle to start anew. At the conclusion of n cycles of extension-recover-deblock-wash, the full length, single strand polydeoxynucleotide will be cleaved from the solid support and isolated for subsequent use. A variety of 3'-O-blocked deoxynucleotides, may be used, but the choice of specific 3'-O-blocking groups is dictated by: 1) the smallest possible bulk to maximize substrate utilization by TdT and 2) removal of the blocking group with the mildest and preferably aqueous conditions in the shortest period of time.

Cost savings by this approach will be achieved by exploiting the higher yield of final oligonucleotide product at a lower starting scale than currently being used as the existing industry standard (i.e., less than 1 nanomole). Future adaptation of this enzymatic approach to array based formats will allow even further and more dramatic reductions in the cost of synthesis of long oligonucleotides achievable by highly parallel synthesis. Furthermore, the enzymatic synthesis process that we propose uses only aqueous based chemistries like buffers and salts, thus greatly reducing the environmental burden of the organic waste generated by the existing phosphoramidite method.

Figure 1:
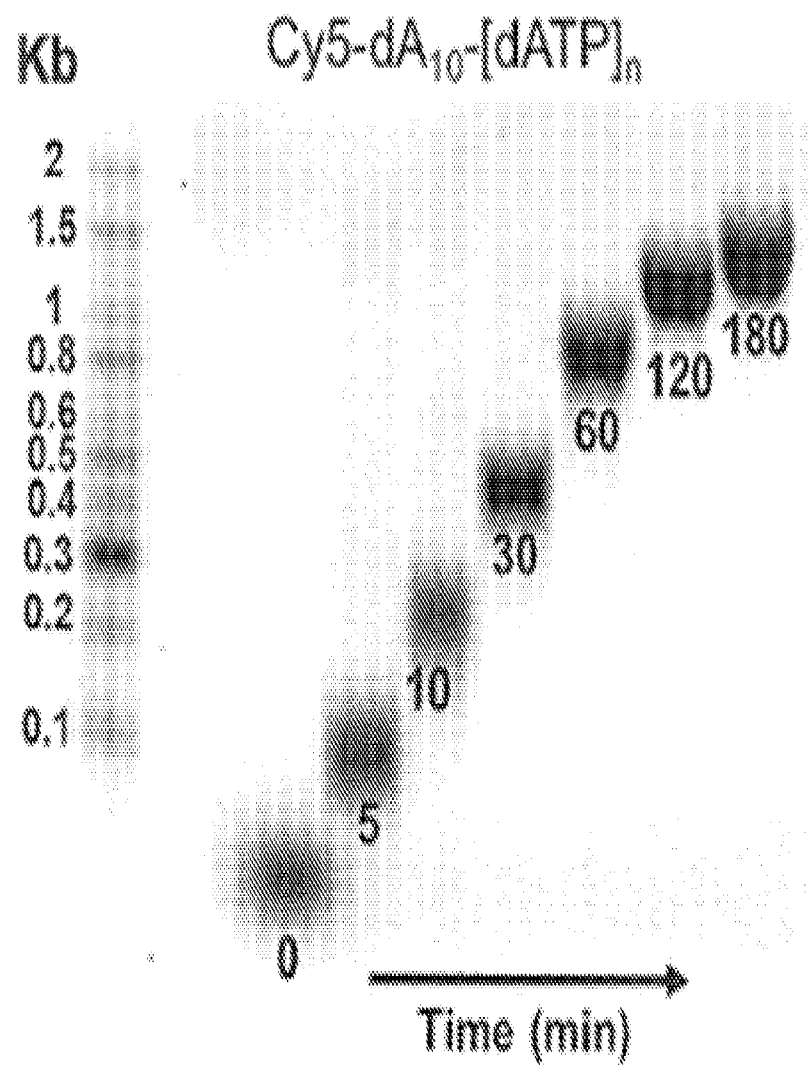
FIG. 1 shows an agarose gel of a solution phase polymerization reaction composed of terminal deoxynucleotidyl transferase (TdT), deoxyadenosine triphosphate (dATP) and fluorescent strand initiator 5'-Cy5-dA10 at different time points from Tjong et al. "Amplified on-chip fluorescence detection of DNA hybridization by surface-initiated enzymatic polymerization," *Anal. Chem.*, 2011; 83:5153-5159 (2011).

The methods of the invention may be used to modify terminal deoxynucleotidyl transferases (TdT), however other enzymes could be modified with similar methods. TdT is likely to be a successful starting enzyme because it is capable of 3'-extension activity using single strand initiating primers in a template-independent polymerization. However, prior to the invention described herein, there have been no reports of 3'-O-blocked nucleotides being incorporated into single-stranded oligonucleotide by an enzyme in the absence of a template. In fact, as Chang and Bollum reported, substitution of the 3'-hydroxyl group results in complete inactivity of available transferase enzymes. See Chang and Bollum, "Molecular Biology of Terminal Transferase, *CRC Critical Reviews in Biochemistry*, vol. 21 (1), p. 27-52 (1986), incorporated herein by reference in its entirety. Nonetheless, when TdT is used with natural dNTPs (i.e., not 3'-O-blocked), and without a template, oligonucleotide extension continues without stopping. Such uncontrolled incorporation is evidenced by the time-dependent gel electrophoresis images shown in FIG. 1. FIG. 1 shows an agarose gel of a solution phase polymerization reaction composed of terminal deoxynucleotidyl transferase (TdT), deoxyadenosine triphosphate (dATP) and fluorescent strand initiator 5'-Cy5-dA10 at different time points. (Adapted with permission from Tjong et al. "Amplified on-chip fluorescence detection of DNA hybridization by surface-initiated enzymatic polymerization," *Anal. Chem.*, 2011; 83:5153-5159 (2011), incorporated by reference herein in its entirety.) Additionally, TdT can extend primers in a near quantitative manner resulting in the addition of thousands of nucleotides, while TdT is likely to accept a wide variety of modified and substituted dNTPs as efficient substrates. Furthermore, a substantial library of mechanistic and structural information regarding TdT already exists. See Delarue et al., *EMBO J.* 2002; 21(3):427-39; Gouge et al., *J Mol Biol.* 2013 Nov. 15; 425(22):4334-52 and Romain et al., *Nucleic Acids Res.* 2009; 37(14):4642-56, both of which are incorporated by reference in their entireties.

It is known that TdT can use substrates having modifications and/or substitutions at the deoxyribose sugar ring as well as the purine/pyrimidine nucleobases. For example, TdT accepts bulky modifications at the C5 of pyrimidines and the C7 of purines. See Sorensen et al., "Enzymatic Ligation of Large Biomolecules to DNA," *ACS Nano* 2013, 7(9):8098-104; Figeys et al., *Anal. Chem.* 1994, 66(23): 4382-3; Li et al., *Cytometry,* 1995, 20(2):172-80, all of which are incorporated by reference in their entireties. In some instances, TdT can even accept non-nucleotide triphosphates. See Barone et al., *Nucleotides and Nucleic Acids* 2001, 20(4-7):1141-5, and Alexandrova et al., *Bioconjug Chem.,* 2007, 18(3):886-93, both of which are incorporated by reference in their entireties. However, there is little evidence in the prior art that TdT can accept 3'-O-blocked nucleotides. See, for example, Knapp et al., *Chem. Eur. J.,* 2011, 17:2903, incorporated herein by reference in its entirety. While the lack of activity of TdT was not a focus of Knapp et al., the authors reported that they tested their 3'-OH modified analog with TdT, and saw no incorporation of this relatively small 3'-OH modification into an oligonucleotide.

Native TdT is a very efficient enzyme. It has been demonstrated that TdT can polymerize extremely long homopolydeoxynucleotides of 1000 to 10,000 nucleotides in length (see Hoard et al., *J of Biol Chem,* 1969 244(19):5363-73; Bollum, *The Enzymes*, Volume 10, New York: Academic Press; 1974. p. 141-71; Tjong et al., *Anal Chem,* 2011, 83:5153-59, all of which are incorporated by reference in their entireties). Random sequence oligomers consisting of all four nucleotides have also been polymerized by TdT, however there are no reports of ordered polynucleotides being synthesized in the absence of a template. See Damiani, et al., *Nucleic Acids Res,* 1982, 10(20):6401-10, incorporated by reference herein in its entirety. Support-bound synthesis of polynucleotides by TdT is additionally supported by reports of homopolymer synthesis of 150 bps initiators covalently attached to self-assembled monolayers on gold surfaces. See Chow et al., *J Am Chem Soc* 2005; 127:14122-3, and Chow and Chilikoti, *Langmuir* 2007, 23:11712-7, both of which are incorporated by reference in their entireties. These authors also observed preference by TdT of dATP>dTTP>>dGTP≈dCTP for incorporation of homopolymers. In a more recent report, Tjong et al. demonstrated the TdT mediated synthesis of long (>1 Kb) homopolymer ssDNA from initiator primers immobilized on glass surfaces.

Figure 3:
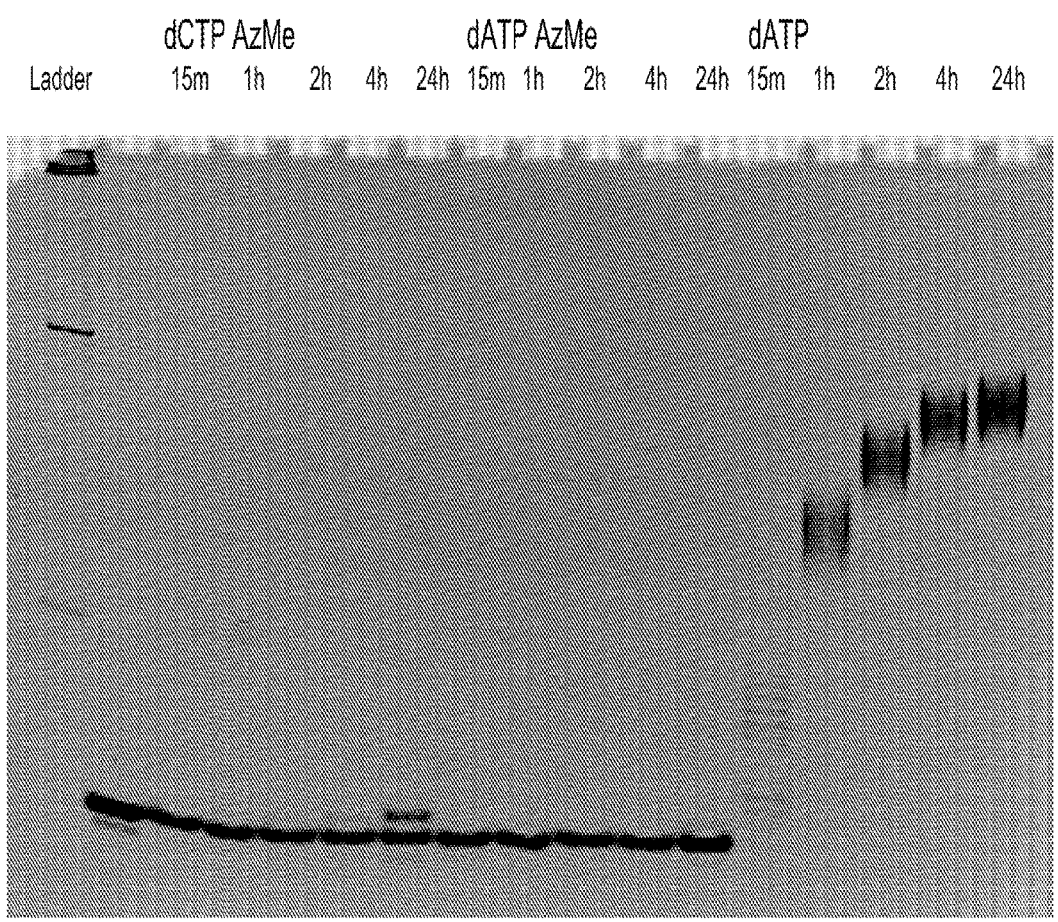
FIG. 3 shows the polyacrylamide gel analysis of a solution phase reaction time course of commercially-available TDT and a nucleic acid initiator with 3'-O-azidomethyl-dCTP or 3'-O-azidomethyl-dATP. Lane 1—100 bp ladder size standard, Lane 2—oligonucleotide standard, Lane 3—3'-O-azidomethyl-dCTP+TdT 15' reaction time, Lane 4—1 hour, Lane 5—2 hours, Lane 6—4 hours, Lane 7—24 hours, Lane 8—3'-O-azidomethyl-dATP+TdT 15' reaction time, Lane 9—1 hour, Lane 10—2 hours, Lane 10—4 hours, Lane 11—24 hours, Lane 12—dATP+TdT 15' reaction time, Lane 13—1 hour, Lane 14—4 hours, Lane 15—24 hours.

The distributive behavior of TdT is reinforced by FIG. 3, which shows a time course of a solution phase synthesis of 1-1.5 kb homopolymers. After each addition of an unmodified (natural) dNTP, the enzyme dissociates, thus allowing the random extension of any strand in the population. The distribution of product lengths in such a system should follow a Poisson distribution, as reported by Bollum and co-workers in 1974. If TdT were used with a terminating nucleotide species, i.e., one with the 3'-O-position blocked, the reaction should proceed to completion, resulting not in a distribution of product lengths, but essentially a pure product of a single nucleotide addition.

Nonetheless, as described above, nucleotide synthesis with 3'-O-blocked dNTPs does not proceed with commercially-available TdT proteins. This fact is reinforced by FIG. 3, which shows a gel shift assay used to monitor the solution phase incorporation kinetics of 3'-O-azidomethyl dATP and 3'-O-azidomethyl dCTP using a commercially-available, recombinant TdT. The data in FIG. 3 clearly show that neither 3'-O-modified dNTP analog is a substrate for TdT, i.e., there is no polynucleotide extension when compared to reactions containing dATP as a positive control (lanes 12 thru 15). FIG. 3, thus, adds further evidence that commercially-available TdTs are not able to synthesize oligomers by incorporating dNTPs with modified 3'-OHs.

With suitable modifications, a variety of different 3'-O-blocked dNTP analogs will be suitable for the controlled addition of nucleotides by TdT. Modified 3'-O-blocked dNTP analogs include, but are not limited to, the 3'-O-allyl, 3'-O-azidomethyl, 3'-O—NH$_2$, and 3'-OCH$_2$CN blocking groups. Overall, the choice of the 3'-O-blocking group will dictated by: 1) the smallest possible bulk to maximize substrate utilization by TdT, which is likely to affect kinetic uptake, and 2) the blocking group with the mildest removal conditions, preferably aqueous, and in the shortest period of time. 3'-O-blocking groups that are the suitable for use with this invention are described in WO 2003/048387; WO 2004/018497; WO 1996/023807; WO 2008/037568; Hutter D, et al. *Nucleosides Nucleotides Nucleic Acids*, 2010, 29(11): 879-95; and Knapp et al., *Chem. Eur. J.*, 2011, 17:2903, all of which are incorporated by reference in their entireties.

Figure 4:
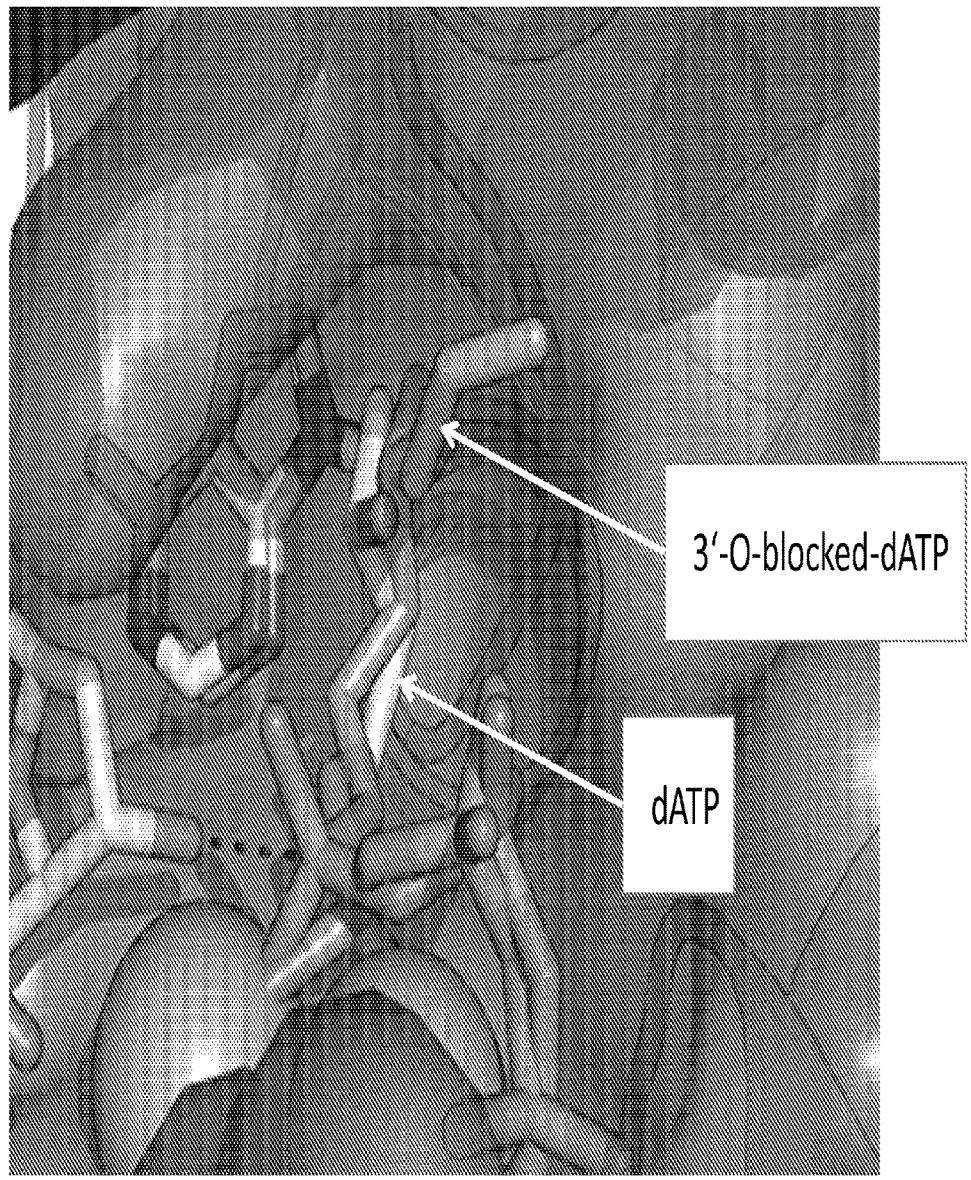
FIG. 4 shows a computer-generated image of the active site of TdT using the PDB crystal structure 1KDH, showing the computationally docked catalytically productive positions of a dATP (white frame) and a 3'-O-allyl-dATP analog (green frame), each complexed to the two active-site metal ions (large pink spheres). The white framework model on the left side of the graphic shows the 3'-OH of the oligonucleotide chain attacking the alpha phosphate (dotted black line) of the incoming dATP or 3'-O-allyl-dATP analog. The deoxyribose (green) wireframe model shows the position of a 3'-O-allyl dATP analog while the deoxyribose (white) wireframe models shows the position of unmodified dATP.

A computational model of the active site of murine TdT was created to understand the structural basis for the lack of utilization of 3'-O-blocked dNTPs by TdT. Additionally, the computer model made it possible to "fit" various modified dNTPs into the active site. FIG. 4 shows the docking of a 3'-O-allyl-dATP (shown in green) with murine TdT (see SEQ ID NO. 9, below) using the PDB crystal structure 1KDH and AutoDock 4.2 (Molecular Graphics Laboratory, Scripps Research Institute, La Jolla, Calif.). FIG. 4 also shows a dATP with an unmodified 3'-OH (white) superimposed on the 3'-O-allyl-dATP. The phosphate portions of the dATPs (orange/red) are in complex with the catalytic metal ions (pink) while the alpha phosphate is positioned to be attacked by the 3'-OH of the bound oligonucleotide initiator (black dotted line). The model shown in FIG. 4 predicts that there is sufficient room for the 3'-allyl-dNTP to interact with TdT in a catalytically productive conformation, but larger protecting groups at this position will likely prevent catalytically-productive binding of such modified dNTP analogs.

AutoDock's predicted binding mode suggests that modification to the 3'-OH will change the electrostatic interactions between two residues, Arg336 and Arg454. Although Arg336 is near the reaction center in the active site, Arg 336 is highly conserved, and early studies found that replacement of Arg336 with Gly or Ala reduced dNTP activity by 10-fold (Yang B et al. J. Mol. Biol. 1994; 269(16):11859-68). Accordingly, one motif for modification is the GGFRR motif including Arg 336 in the above structural model.

On the other hand, sequence analysis of the TdT family demonstrates a wide range of amino acids that can be accommodated at position 454. This analysis suggests structural flexibility at position 454, and surrounding residues. Additionally, it is thought that Gly452 and Ser453 exist in a cis-peptide bond conformation (see Delarue et al., *EMBO J.*, 2002; 21(3):427-39, incorporated herein by reference in its entirety) and that the guanidinium group of Arg336 assists in the stabilization of this conformation. The stability provided by Arg336 may help explain why substitutions at this position have a negative impact on the reactivity of modified TdT proteins. In some instances, the instability created by modifying position 336 may be overcome by using proline residues to stabilize cis-peptide bond conformation. However, if Arg336 is substituted, e.g., with alanine or glycine, the entire TGSR motif (positions 451, 452, 435, 454) may also have to be modified to compensate for this change. For example, the TGSR motif may be modified to TPSR or TGPR. Accordingly, the TGSR motif, including Gly452 in the above structural model was targeted for modification.

In another embodiment, substitutions at Arg454 to accommodate the steric bulk of a 3'-O-blocking group may require additional modifications to the α14 region to compensate for substitutions of glycine or alanine at Arg454. In other embodiments, substitutions to other residues in the α11 region may be required to compensate for substitution to Arg336 either instead of, or in addition to, modification of the TGSR motif.

Figure 5:
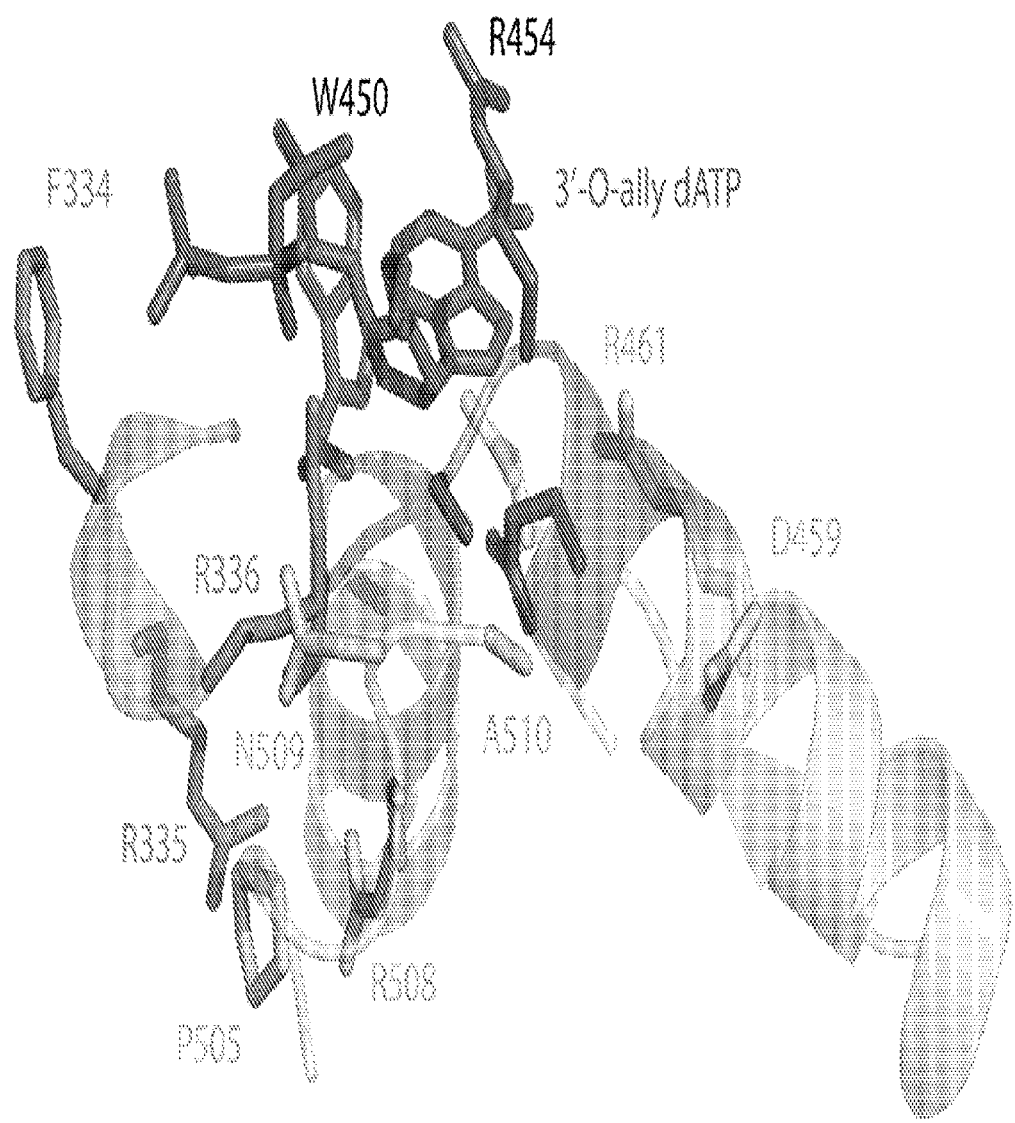
FIG. 5 shows a ribbon model of the active site of TdT using the PDB crystal structure 1KDH with a computationally docked catalytically productive 3'-O-allyl dATP analog showing the amino acid residues in closest proximity to the 3'-O of the ligand. These residues may be modified to create mutant TdTs suitable for use with the invention.

While modification to Arg336 and Arg454 may change the binding interactions of 3'-O-modified dNTPs, it may also be necessary to explore substitutions that would result in improved steric interactions of 3'-O-modified dNTPs with TdT. Such steric modifications can also be explored computationally. FIG. 5 shows a model of a catalytically-productive, docked 3'-O-allyl modified dATP and its interactions with residues such as Gly332, Gly333, Gly452, Thr451 and Ser453 of murine TdT. Each of these residues is within 0.6 nm of the 3'-OH of a typical dNTP. These residues are also potential targets for substitution to allow the extra steric bulk of a 3'-blocking group like 3'-O-azidomethyl or 3'-O-allyl. Residues that are within 1.2 nm of the 3'-OH such as Glu457, Ala510, Asp509, Arg508, Lys199, Ser196 Met192, or Leu161 may also potentially interfere with the substrate utilization of a 3'-O-blocked dNTP and are thus targets for substitution in addition to or in combination with Arg336 and Arg454. In addition to amino acid substitutions at positions 508, 509 and 510 it may be necessary to delete residues to remove interference with a 3'-O-blocking group such as deletions of one or more amino acids between Pro505 and Asp509. Other residues that may need to be altered are Val 436, Trp450, Ser453, Phe456, Glu491, Phe495. In some embodiments, the following changes may be required: Arg454Ala, Arg454Gly, Trp450Gly, Trp450A, Thr451Gly, Thr451Ala, Glu491Asp, Ser453Ala, Ser453Gly, Trp450His, Trp450Tyr, Trp450Phe. Combinations of changes like Trp450Ala+Val436Trp, Phe456Tyr+Phe495Tyr may be required to remove interference with a 3'-O-blocking group. Since these amino acids are located near the C-terminus of the protein, and exist in a relatively unstructured region, they may be deleted singly or altogether, either instead of or in combination with the modifications described above.

As shown below, most TdTs include the GGFRR and TGSR motifs. In the following sequences, the GGFRR and TGSR motifs have been bolded and underlined for easy reference. Native calf thymus TdT is a candidate for alteration of the primary structure to achieve a suitable template-independent polymerase. However, a variety of other proteins may be explored to identify a candidate suitable for the use with 3'-O-blocked dNTP analogs, including human and murine TdT. The amino acid sequence corresponding to native calf TdT is listed in Table 1 as SEQ ID NO. 1, while the nucleic acid sequence is listed in Table 2 as SEQ ID NO. 2. In some embodiments, the resulting protein, adapted for sequence-specific de novo polynucleotide synthesis with 3'-O-modified dNTPs and NTPs, will be at least 85% identical, i.e., at least 90% identical, i.e., at least 93% identical, i.e., at least 95% identical, i.e., at least 97% identical, i.e., at least 98% identical, i.e., at least 99% identical, with SEQ ID NO. 1. Furthermore, it may be possible to truncate portions of the amino acid sequence of bovine TdT and still maintain catalytic activity.

TABLE 1

Amino Acid Sequence of Bovine TdT

SEQ ID NO. 1: (520 aa)
MAQQRQHQRL PMDPLCTASS GPRKKRPRQV GASMASPPHD

IKFQNLVLFI LEKKMGTTRR NFLMELARRK GFRVENELSD

SVTHIVAENN SGSEVLEWLQ VQNIRASSQL ELLDVSWLIE

SMGAGKPVEI TGKHQLVVRT DYSATPNPGF QKTPPLAVKK

ISQYACQRKT TLNNYNHIFT DAFEILAENS EFKENEVSYV

TFMRAASVLK SLPFTIISMK DTEGIPCLGD KVKCIIEEII

EDGESSEVKA VLNDERYQSF KLFTSVFGVG LKTSEKWFRM

GFRSLSKIMS DKTLKFTKMQ KAGFLYYEDL VSCVTRAEAE

AVGVLVKEAV WAFLPDAFVT MTGGFRRGKK IGHDVDFLIT

SPGSAEDEEQ LLPKVINLWE KKGLLLYYDL VESTFEKFKL

PSRQVDTLDH FQKCFLILKL HHQRVDSSKS NQQEGKTWKA

IRVDLVMCPY ENRAFALLGW TGSRQFERDI RRYATHERKM

MLDNHALYDK TKRVFLKAES EEEIFAHLGL DYIEPWERNA

TABLE 2

Nucleic Acid Sequence of Bovine TdT

SEQ ID NO. 2: (1923 nt)
ctcttctgga gataccactt gatggcacag cagaggcagc atcagcgtct tcccatggat ccgctgtgca cagcctcctc aggccctcgg aagaagagac ccaggcaggt gggtgcctca atggcctccc ctcctcatga catcaagttt caaaatttgg tcctcttcat tttggagaag aaatgggaa ccacccgcag TABLE 2-continued Nucleic Acid Sequence of Bovine TdT aaacttcctc atggagctgg ctcgaaggaa aggtttcagg gttgaaaatg agctcagtga ttctgtcacc cacattgtag cagaaaacaa ctctggttca gaggttctcg agtggcttca ggtacagaac ataagagcca gctcgcagct agaactcctt gatgtctcct ggctgatcga aagtatggga gcaggaaaac cagtggagat tacaggaaaa caccagcttg ttgtgagaac agactattca gctacccaa acccaggctt ccagaagact ccaccacttg ctgtaaaaaa gatctcccag tacgcgtgtc aaagaaaaac cactttgaac aactataacc acatattcac ggatgccttt gagatactgg ctgaaaattc tgagtttaaa gaaaatgaag tctcttatgt gacatttatg agagcagctt ctgtacttaa atctctgcca ttcacaatca tcagtatgaa ggatacagaa ggaattccct gcctggggga caaggtgaag tgtatcatag aggaaattat tgaagatgga gaaagttctg aagttaaagc tgtgttaaat gatgaacgat atcagtcctt caaactcttt acttctgttt ttggagtggg actgaagaca tctgagaaat ggttcaggat ggggttcaga tctctgagta aaataatgtc agacaaaacc ctgaaattca caaaaatgca gaaagcagga tttctctatt atgaagacct tgtcagctgc gtgaccaggg ccgaagcaga ggcggttggc gtgctggtta aagaggctgt gtgggcattt ctgccggatg cctttgtcac catgacagga ggattccgca ggggtaagaa gattgggcat gatgtagatt ttttaattac cagcccagga tcagcagagg atgaagagca acttttgcct aaagtgataa acttatggga aaaaaaggga ttacttttat attatgacct tgtggagtca acatttgaaa agttcaagtt gccaagcagg caggtggata ctttagatca ttttcaaaaa tgctttctga ttttaaaatt gcaccatcag agagtagaca gtagcaagtc caaccagcag gaaggaaaga cctggaaggc catccgtgtg gacctggtta tgtgcccta cgagaaccgt gcctttgccc tgctaggctg gactggctcc cggcagtttg agagagacat ccggcgctat gccacacacg agcggaagat gatgctggat aaccacgctt tatatgacaa gaccaagagg gtatttctca agcggaaag tgaagaagaa atctttgcac atctgggatt ggactacatt gaaccatggg aaagaaatgc ttaggagaaa gctgtcaact tttttctttt ctgttctttt tttcaggtta gacaaattat gcttcatatt ataatgaaag atgccttagt caagtttggg attctttaca ttttaccaag atgtagattg cttctagaaa taagtagttt tggaaacgtg atcaggcacc ccctgggtta TABLE 2-continued Nucleic Acid Sequence of Bovine TdT tgctctggca agccatttgc aggactgatg tgtagaactc gcaatgcatt ttccatagaa acagtgttgg aattggtggc tcatttccag ggaagttcat caaagcccac tttgcccaca gtgtagctga aatactgtat acttgccaat aaaaatagga aac Additionally, to make isolation of recombinant proteins easier, it is common to append an N-terminal His tag sequence to the recombinant protein (see Boule J-B et al., *Molecular Biotechnology*, 1998; 10:199-208, incorporated by reference herein in its entirety), which is used in combination with an affinity column (Hitrap, Amersham Pharmacia Biotech, Uppsala, Sweden). Alternatively, N-terminal truncated forms of the enzyme with appended His-tag sequence will work with the current invention (see, e.g., U.S. Pat. No. 7,494,797, incorporated by reference herein in its entirety). His-tagged Bovine TdT amino acid sequences are shown below in Tables 3, 5, and 7, while His-tagged Bovine TdT nucleic acid sequences are shown below in Tables 4, 6, and 8. His tags may be engineered at other positions as required. In some embodiments, the resulting protein, adapted for sequence-specific de novo polynucleotide synthesis with 3'-O-modified dNTPs and NTPs, will be at least 85% identical, i.e., at least 90% identical, i.e., at least 93% identical, i.e., at least 95% identical, i.e., at least 97% identical, i.e., at least 98% identical, i.e., at least 99% identical, with SEQ ID NOS. 3, 5, or 7.

TABLE 3

Amino Acid Sequence of a t-138 and
His-tagged Bovine TdT.

SEQ ID No. 3: (392 aa)
Met Arg Gly Ser His His His His His His Arg Thr

Asp Tyr Ser Ala Thr Pro Asn Pro Gly Phe Gln Lys

Thr Pro Pro Leu Ala Val Lys Lys Ile Ser Gln Tyr

Ala Cys Gln Arg Lys Thr Thr Leu Asn Asn Tyr Asn

His Ile Asp Ala Phe Glu Ile Leu Ala Glu Asn Ser

Glu Phe Lys Glu Asn Glu Val Ser Tyr Val Thr Phe

Met Arg Ala Ala Ser Val Leu Lys Ser Leu Pro Phe

Thr Ile Ile Ser Met Lys Asp Thr Phe Thr Glu Gly

Ile Pro Cys Leu Gly Asp Lys Val Lys Cys Ile Ile

Glu Glu Ile Ile Glu Asp Gly Glu Ser Ser Glu Val

Lys Ala Val Leu Asn Asp Glu Arg Tyr Gln Ser Phe

Lys Leu Ser Val Phe Gly Val Gly Leu Lys Thr Ser

Glu Lys Trp Phe Arg Met Gly Phe Thr Phe Arg Ser

Leu Ser Lys Ile Met Ser Asp Lys Thr Leu Lys Lys

Met Gln Lys Ala Gly Phe Leu Tyr Tyr Glu Asp Leu

Val Ser Cys Val Thr Arg Ala Glu Ala Glu Ala Val

TABLE 3-continued

Amino Acid Sequence of a t-138 and
His-tagged Bovine TdT.

Gly Val Leu Val Lys Glu Ala Val Trp Ala Phe Leu

Pro Asp Ala Phe Val Thr Met Thr Gly Gly Phe Arg

Arg Gly Lys Lys Ile Gly His Asp Val Asp Phe Leu

Ile Thr Ser Pro Gly Ser Ala Glu Asp Glu Glu Gln

Leu Leu Pro Lys Val Ile Asn Leu Trp Glu Lys Lys

Gly Leu Leu Leu Tyr Tyr Asp Leu Val Glu Ser Thr

Phe Glu Lys Phe Lys Phe Thr Leu Pro Ser Arg Gln

Val Asp Thr Leu Asp His Phe Gln Lys Cys Phe Leu

Ile Leu Lys Leu His His Gln Arg Val Asp Ser Ser

Lys Ser Asn Gln Gln Glu Gly Lys Thr Trp Lys Ala

Ile Arg Val Asp Leu Val Met Cys Pro Tyr Glu Asn

Arg Ala Phe Ala Leu Leu Gly Trp Thr Gly Ser Arg

Gln Phe Glu Arg Asp Ile Arg Arg Tyr Ala Thr His

Glu Arg Lys Met Met Leu Asp Asn His Ala Leu Tyr

Asp Lys Thr Lys Arg Val Phe Leu Lys Ala Glu Ser

Glu Glu Glu Ile Phe Ala His Leu Gly Leu Asp Tyr

Ile Glu Pro Trp Glu Arg Asn Ala

TABLE 4

Nucleotide Sequence of a t-138 and
His-tagged Bovine TdT.

SEQ ID No. 4: (1187 nt)
atgagaggat cgcatcacca tcaccatcac agaacagact attcagctac cccaaaccca ggcttccaga agactccacc acttgctgta aaaagatct cccagtacgc gtgtcaaaga aaaaccactt tgaacaacta taccacata ttcacggatg cctttgagat actggctgaa aattctgagt ttaaagaaaa tgaagtctct tatgtgacat ttatgagagc agcttctgta cttaaatctc tgccattcac aatcatcagt atgaaggata cagaaggaat tccctgcctg ggggacaagg tgaagtgtat catagaggaa attattgaag atggagaaag ttctgaagtt aaagctgtgt taaatgatga acgatatcag tccttcaaac tctttacttc tgttttttgga gtgggactga agacatctga gaaatggttc aggatggggt tcagatctct gagtaaaata atgtcagaca aaaccctgaa attcacaaaa atgcagaaag caggatttct ctattatgaa gaccttgtca gctgcgtgac cagggccgaa gcagaggcgg ttggcgtgct ggttaaagag gctgtgtggg catttctgcc ggatgccttt gtcaccatga caggaggatt ccgcaggggt aagaagattg gcatgatgt TABLE 4-continued Nucleotide Sequence of a t-138 and His-tagged Bovine TdT.

agatttttta attaccagcc caggatcagc agaggatgaa
gagcaacttt tgcctaaagt gataaactta tgggaaaaaa
agggattact tttatattat gaccttgtgg agtcaacatt
tgaaaagttc aagttgccaa gcaggcaggt ggatacttta
gatcattttc aaaaatgctt tctgatttta aaattgcacc
atcagagagt agacagtagc aagtccaacc agcaggaagg
aaagacctgg aaggccatcc gtgtggacct ggttatgtgc
ccctacgaga accgtgcctt tgccctgcta ggctggactg
gctcccggca gtttgagaga catccggc gctatgccac
acacgagcgg aagatgatgc tggataacca cgctttatat
gacaagacca gagggtatt tctcaaagcg gaaagtgaag
aagaaatctt tgcacatctg ggattggact acattgaacc
atgggaaaga aatgcttaag cttgcgc

TABLE 5

Amino Acid Sequence of a t-151 and His-tagged Bovine TdT.

SEQ ID No. 5: (379 aa)
Met Arg Gly Ser His His His His His His Lys Thr
Pro Pro Leu Ala Val Lys Lys Ile Ser Gln Tyr Ala
Cys Gln Arg Lys Thr Thr Leu Asn Asn Tyr Asn His
Ile Asp Ala Phe Glu Ile Leu Ala Glu Asn Ser Glu
Phe Lys Glu Asn Glu Val Ser Tyr Val Thr Phe Met
Arg Ala Ala Ser Val Leu Lys Ser Leu Pro Phe Thr
Ile Ile Ser Met Lys Asp Thr Phe Thr Glu Gly Ile
Pro Cys Leu Gly Asp Lys Val Lys Cys Ile Ile Glu
Glu Ile Ile Glu Asp Gly Glu Ser Ser Glu Val Lys
Ala Val Leu Asn Asp Glu Arg Tyr Gln Ser Phe Lys
Leu Ser Val Phe Gly Val Gly Leu Lys Thr Ser Glu
Lys Trp Phe Arg Met Gly Phe Thr Phe Arg Ser Leu
Ser Lys Ile Met Ser Asp Lys Thr Leu Lys Lys Met
Gln Lys Ala Gly Phe Leu Tyr Tyr Glu Asp Leu Val
Ser Cys Val Thr Arg Ala Glu Ala Glu Ala Val Gly
Val Leu Val Lys Glu Ala Val Trp Ala Phe Leu Pro
Asp Ala Phe Val Thr Met Thr Gly Gly Phe Arg Arg
Gly Lys Lys Ile Gly His Asp Val Asp Phe Leu Ile
Thr Ser Pro Gly Ser Ala Glu Asp Glu Glu Gln Leu
Leu Pro Lys Val Ile Asn Leu Trp Glu Lys Lys Gly
Leu Leu Leu Tyr Tyr Asp Leu Val Glu Ser Thr Phe

TABLE 5-continued

Amino Acid Sequence of a t-151 and His-tagged Bovine TdT.

Glu Lys Phe Lys Phe Thr Leu Pro Ser Arg Gln Val
Asp Thr Leu Asp His Phe Gln Lys Cys Phe Leu Ile
Leu Lys Leu His His Gln Arg Val Asp Ser Ser Lys
Ser Asn Gln Gln Glu Gly Lys Thr Trp Lys Ala Ile
Arg Val Asp Leu Val Met Cys Pro Tyr Glu Asn Arg
Ala Phe Ala Leu Leu Gly Trp Thr Gly Ser Arg Gln
Phe Glu Arg Asp Ile Arg Arg Tyr Ala Thr His Glu
Arg Lys Met Met Leu Asp Asn His Ala Leu Tyr Asp
Lys Thr Lys Arg Val Phe Leu Lys Ala Glu Ser Glu
Glu Glu Ile Phe Ala His Leu Gly Leu Asp Tyr Ile
Glu Pro Trp Glu Arg Asn Ala

TABLE 6

Nucleotide Sequence of a t-151 and His-tagged Bovine TdT.

SEQ ID No. 6: (1148 nt)
atgagaggat cgcatcacca tcaccatcac aagactccac
cacttgctgt aaaaaagatc tcccagtacg cgtgtcaaag
aaaaccact tgaacaact ataaccacat attcacggat
gcctttgaga tactggctga aaattctgag tttaaagaaa
atgaagtctc ttatgtgaca tttatgagag cagcttctgt
acttaaatct ctgccattca caatcatcag tatgaaggat
acagaaggaa ttccctgcct ggggacaag gtgaagtgta
tcatagagga aattattgaa gatggagaaa gttctgaagt
taaagctgtg ttaaatgatg aacgatatca gtccttcaaa
ctctttactt ctgtttttgg agtgggactg aagacatctg
agaaatggtt caggatgggg ttcagatctc tgagtaaaat
aatgtcagac aaaaccctga aattcacaaa aatgcagaaa
gcaggatttc tctattatga gaccttgtc agctgcgtga
ccaggccga agcagaggcg gttggcgtgc tggttaaaga
ggctgtgtgg gcatttctgc cggatgcctt tgtcaccatg
acaggaggat tccgcagggg taagaagatt gggcatgatg
tagatttttt aattaccagc ccaggatcag cagaggatga
agcaactt tgcctaaag tgataaactt atgggaaaaa
aagggattac ttttatatta tgaccttgtg gagtcaacat
ttgaaaagtt caagttgcca gcaggcagg tggatacttt
agatcatttt caaaaatgct ttctgatttt aaaattgcac
catcagagag tagacagtag caagtccaac cagcaggaag
gaaagacctg gaaggccatc cgtgtggacc tggttatgtg

TABLE 6-continued

Nucleotide Sequence of a t-151 and His-tagged Bovine TdT.

ccoctacgag aaccgtgcct ttgccctgct aggctggact ggctcccggc agtttgagag agacatccgg cgctatgcca cacacgagcg aaagatgatg ctggataacc acgctttata tgacaagacc aagagggtat ttctcaaagc ggaaagtgaa gaagaaatct ttgcacatct gggattggac tacattgaac catgggaaag aaatgcttaa gcttgcgc

TABLE 7

Amino Acid Sequence of a t-160 and His-tagged Bovine TdT.

SEQ ID No. 7: (370 aa)
Met Arg Gly Ser His His His His His His Ile Ser
Gln Tyr Ala Cys Gln Arg Lys Thr Thr Leu Asn Asn
Tyr Asn His Ile Asp Ala Phe Glu Ile Leu Ala Glu
Asn Ser Glu Phe Lys Glu Asn Glu Val Ser Tyr Val
Thr Phe Met Arg Ala Ala Ser Val Leu Lys Ser Leu
Pro Phe Thr Ile Ile Ser Met Lys Asp Thr Phe Thr
Glu Gly Ile Pro Cys Leu Gly Asp Lys Val Lys Cys
Ile Ile Glu Glu Ile Ile Glu Asp Gly Glu Ser Ser
Glu Val Lys Ala Val Leu Asn Asp Glu Arg Tyr Gln
Ser Phe Lys Leu Ser Val Phe Gly Val Gly Leu Lys
Thr Ser Glu Lys Trp Phe Arg Met Gly Phe Thr Phe
Arg Ser Leu Ser Lys Ile Met Ser Asp Lys Thr Leu
Lys Lys Met Gln Lys Ala Gly Phe Leu Tyr Tyr Glu
Asp Leu Val Ser Cys Val Thr Arg Ala Glu Ala Glu
Ala Val Gly Val Leu Val Lys Glu Ala Val Trp Ala
Phe Leu Pro Asp Ala Phe Val Thr Met Thr Gly Gly Phe Arg Arg Gly Lys Lys Ile Gly His Asp Val Asp
Phe Leu Ile Thr Ser Pro Gly Ser Ala Glu Asp Glu
Glu Gln Leu Leu Pro Lys Val Ile Asn Leu Trp Glu
Lys Lys Gly Leu Leu Leu Tyr Tyr Asp Leu Val Glu
Ser Thr Phe Glu Lys Phe Lys Phe Thr Leu Pro Ser
Arg Gln Val Asp Thr Leu Asp His Phe Gln Lys Cys
Phe Leu Ile Leu Lys Leu His His Gln Arg Val Asp
Ser Ser Lys Ser Asn Gln Gln Glu Gly Lys Thr Trp
Lys Ala Ile Arg Val Asp Leu Val Met Cys Pro Tyr
Glu Asn Arg Ala Phe Ala Leu Leu Gly Trp Thr Gly Ser Arg Gln Phe Glu Arg Asp Ile Arg Arg Tyr Ala
Thr His Glu Arg Lys Met Met Leu Asp Asn His Ala

TABLE 7-continued

Amino Acid Sequence of a t-160 and His-tagged Bovine TdT.

Leu Tyr Asp Lys Thr Lys Arg Val Phe Leu Lys Ala

Glu Ser Glu Glu Glu Ile Phe Ala His Leu Gly Leu

Asp Tyr Ile Glu Pro Trp Glu Arg Asn Ala

TABLE 8

Nucleotide Sequence of a t-160 and His-tagged Bovine TdT.

SEQ ID No. 8: (1121 nt)
atgagaggat cgcatcacca tcaccatcac atctcccagt acgcgtgtca agaaaaaacc actttgaaca actataacca catattcacg gatgcctttg agatactggc tgaaaattct gagtttaaag aaaatgaagt ctcttatgtg acatttatga gagcagcttc tgtacttaaa tctctgccat tcacaatcat cagtatgaag gatacagaag gaattcctg cctgggggac aaggtgaagt gtatcataga ggaaattatt gaagatggag aaagttctga gttaaagct gtgttaaatg atgaacgata tcagtccttc aaactcttta cttctgtttt tggagtggga ctgaagacat ctgaaaatg gttcaggatg gggttcgat ctctgagtaa ataatgtca gacaaaaccc tgaaattcac aaaaatgcag aaagcaggat ttctctatta tgaagacctt gtcagctgcg tgaccagggc cgaagcagag gcggttggcg tgctggttaa agaggctgtg tgggcatttc tgccggatgc ctttgtcacc atgacaggag gattccgcag gggtaagaag attgggcatg atgtagattt tttaattacc agcccaggat cagcagagga tgaagagcaa cttttgccta aagtgataaa cttatgggaa aaaaagggat tacttttata ttatgacctt gtggagtcaa catttgaaaa gttcaagttg ccaagcaggc aggtggatac tttagatcat ttcaaaaat gctttctgat tttaaaattg caccatcaga gagtagacag tagcaagtcc aaccagcagg aaggaaagac ctgaaggcc atccgtgtgg acctggttat gtgcccctac gagaaccgtg cctttgccct gctaggctgg actggctccc ggcagtttga gagagacatc cggcgctatg ccacacacga gcggaagatg atgctggata accacgcttt atatgacaag accaagaggg tatttctcaa agcggaaagt gaagaagaaa tctttgcaca tctgggattg gactacattg aaccatggga agaaatgct taagcttgcg c

TABLE 9

Amino Acid Sequence of murine TdT

```
SEQ ID NO. 9: (510 aa)
MDPLQAVHLG  PRKKRPRQLG  TPVASTPYDI  RFRDLVLFIL

EKKMGTTRRA  FLMELARRKG  FRVENELSDS  VTHIVAENNS

GSDVLEWLQL  QNIKASSELE  LLDISWLIEC  MGAGKPVEMM

GRHQLVVNRN  SSPSPVPGSQ  NVPAPAVKKI  SQYACQRRTT

LNNYNQLFTD  ALDILAENDE  LRENEGSCLA  FMRASSVLKS

LPFPITSMKD  TEGIPCLGDK  VKSIIEGIIE  DGESSEAKAV

LNDERYKSFK  LFTSVFGVGL  KTAEKWFRMG  FRTLSKIQSD

KSLRFTQMQK  AGFLYYEDLV  SCVNRPEAEA  VSMLVKEAVV

TFLPDALVTM  TGGFRRGKMT  GHDVDFLITS  PEATEDEEQQ

LLHKVTDFWK  QQGLLLYCDI  LESTFEKFKQ  PSRKVDALDH

FQKCFLILKL  DHGRVHSEKS  GQQEGKGWKA  IRVDLVMCPY

DRRAFALLGW  TGSRQFERDL  RRYATHERKM  MLDNHALYDR

TKRVFLEAES  EEEIFAHLGL  DYIEPWERNA
```

A variety of 3'-O-modified dNTPs and NTPs may be used with the disclosed proteins for de novo synthesis. In some embodiments, the preferred removable 3'-O-blocking group is a 3'-O-amino, a 3'-O-allyl or a 3'-O-azidomethyl. In other embodiments, the removable 3'-O-blocking moiety is selected from the group consisting of O-phenoxyacetyl; O-methoxyacetyl; O-acetyl; O-(p-toluene)-sulfonate; O-phosphate; O-nitrate; O-[4-methoxy]-tetrahydrothiopyranyl; O-tetrahydrothiopyranyl; O-[5-methyl]-tetrahydrofuranyl; O-[2-methyl,4-methoxy]-tetrahydropyranyl; O-[5-methyl]-tetrahydropyranyl; and O-tetrahydrothiofuranyl (see U.S. Pat. No. 8,133,669). In other embodiments the removable blocking moiety is selected from the group consisting of esters, ethers, carbonitriles, phosphates, carbonates, carbamates, hydroxylamine, borates, nitrates, sugars, phosphoramide, phosphoramidates, phenylsulfenates, sulfates, sulfones and amino acids (see Metzker M L et al. Nuc Acids Res. 1994; 22(20):4259-67, U.S. Pat. Nos. 5,763,594, 6,232,465, 7,414,116; and 7,279,563, all of which are incorporated by reference in their entireties).

Synthesis of Exemplary 3'-O-Blocked dNTP Analogs

Figure 6:
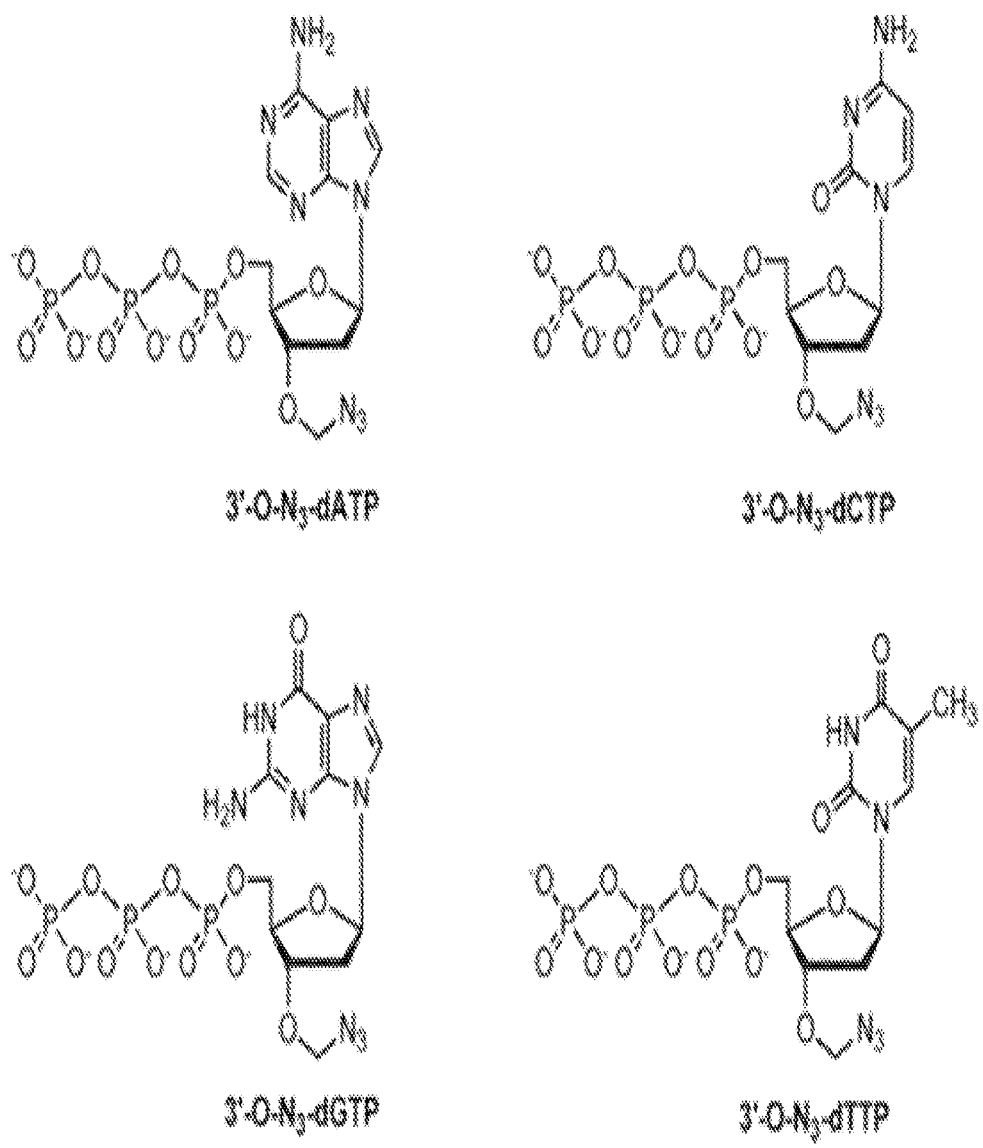
FIG. 6 shows exemplary 3'-O-azidomethyl deoxynucleotides that can be used to synthesize custom DNA oligomers using modified TdTs, as described herein.

FIG. 6 shows four exemplary 3'-O-blocked dNTP analogs, namely 3'-O-azidomethyl-dATP, 3'-O-azidomethyl-dCTP, 3'-O-azidomethyl-dGTP, and 3'-O-azidomethyl-dTTP. The synthesis of each 3'-O-azidomethyl analog is described below and detailed in FIGS. 7-10. The 3'-O-blocked dNTP analogs can also be purchased from specialty suppliers, such as Azco Biotech, Oceanside, Calif. It is to be understood that corresponding 3'-O-blocked ribonucleotides can be formed with similar synthetic methods to enable the creation of custom RNA oligos.

3'-O-azidomethyl-dATP

Figure 7:
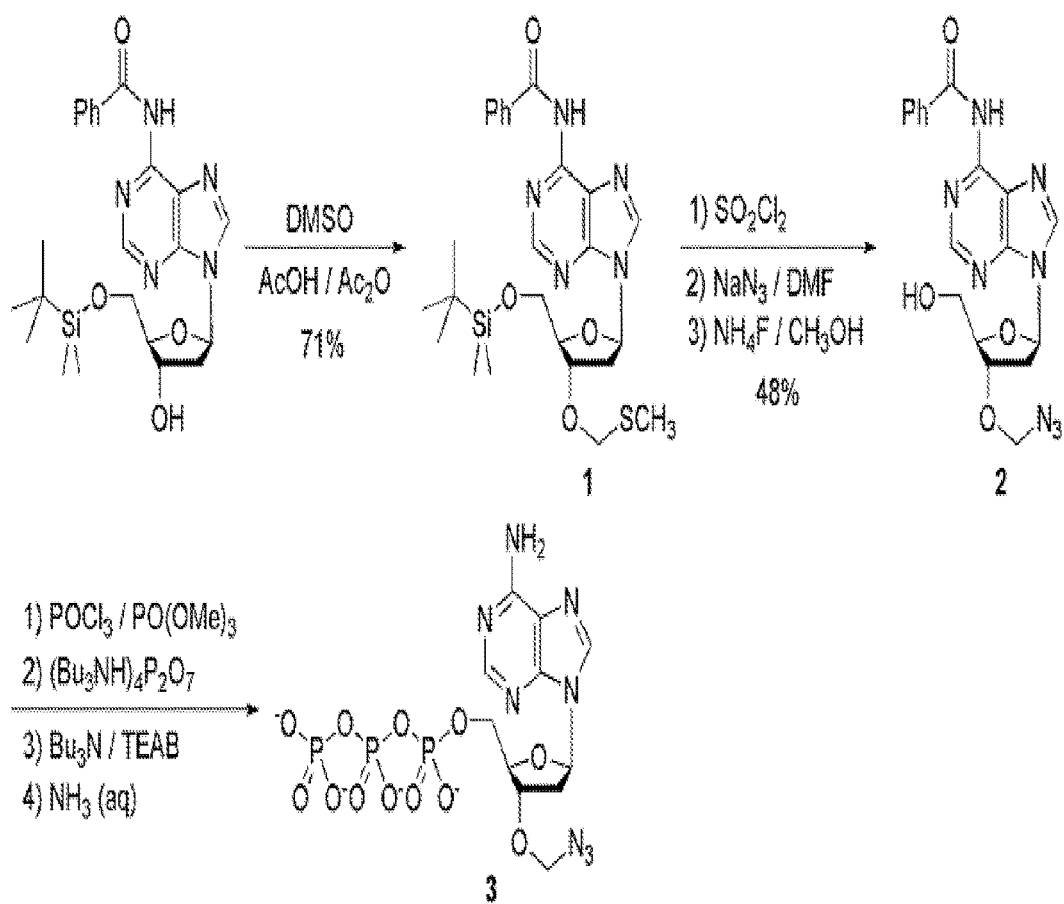
FIG. 7 shows a synthetic scheme for producing 3'-O-azidomethyl deoxyadenosine triphosphate (3'-O-azidomethyl-dATP).
Figure 8:
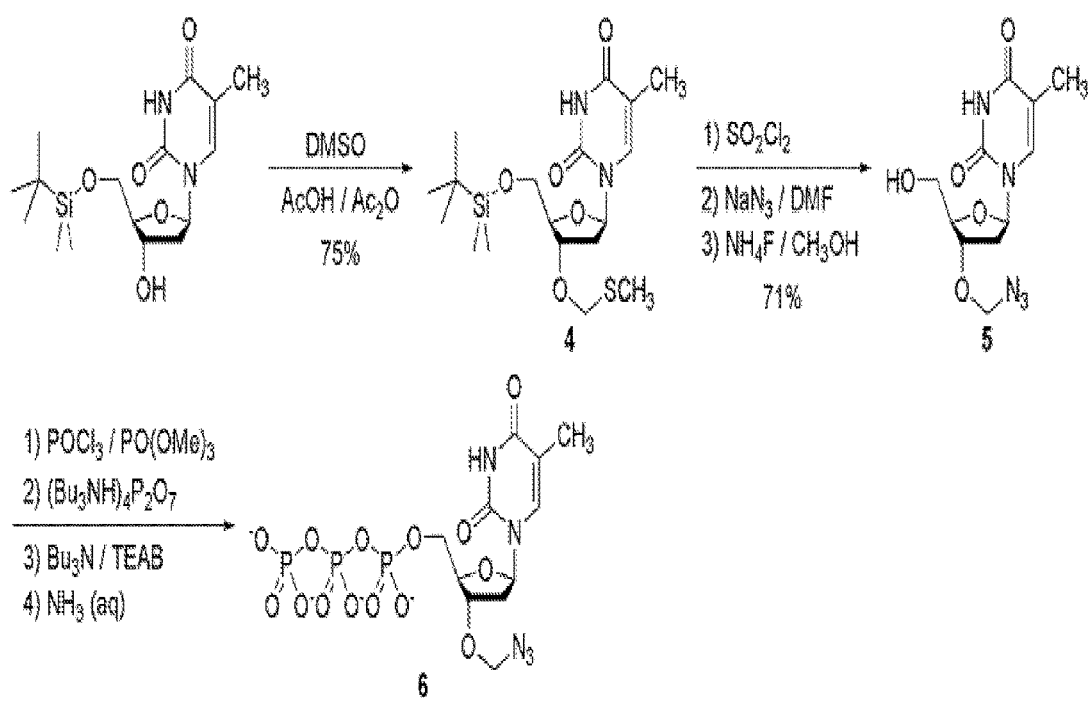
FIG. 8 shows a synthetic scheme for producing 3'-O-azidomethyl deoxythymidine triphosphate (3'-O-azidomethyl-dTTP).
Figure 9:
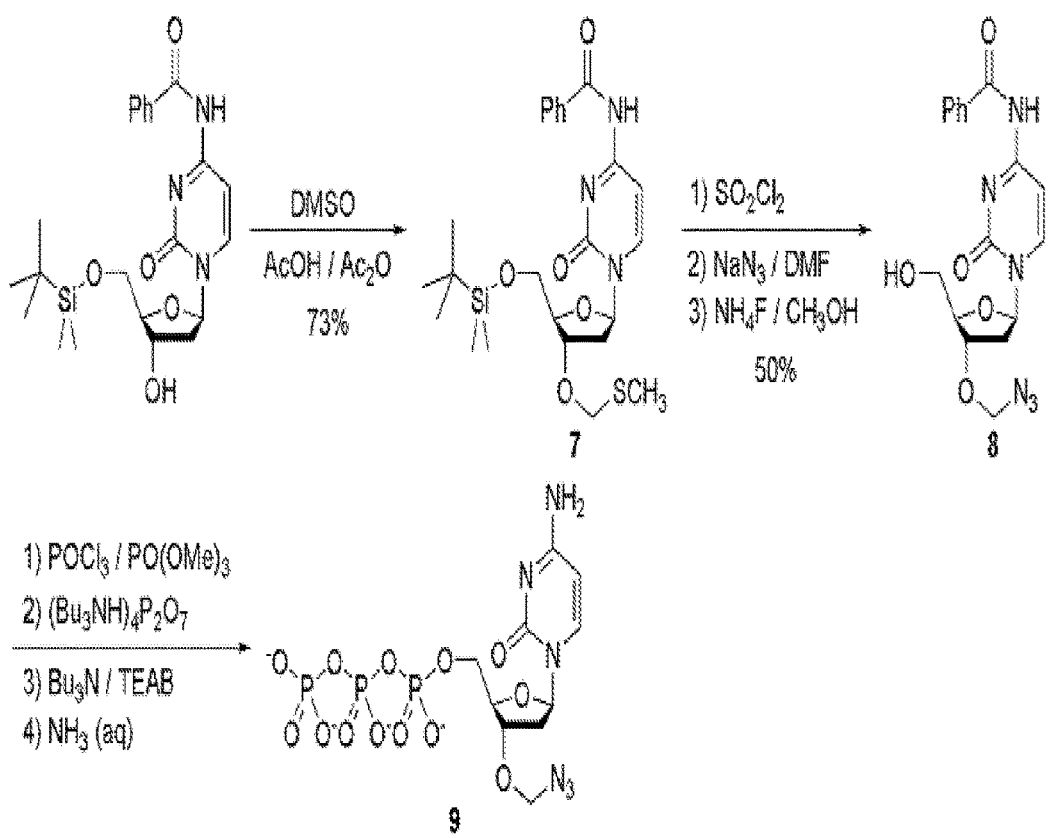
FIG. 9 shows a synthetic scheme for producing 3'-O-azidomethyl deoxycytidine triphosphate (3'-O-azidomethyl-dCTP).
Figure 10:
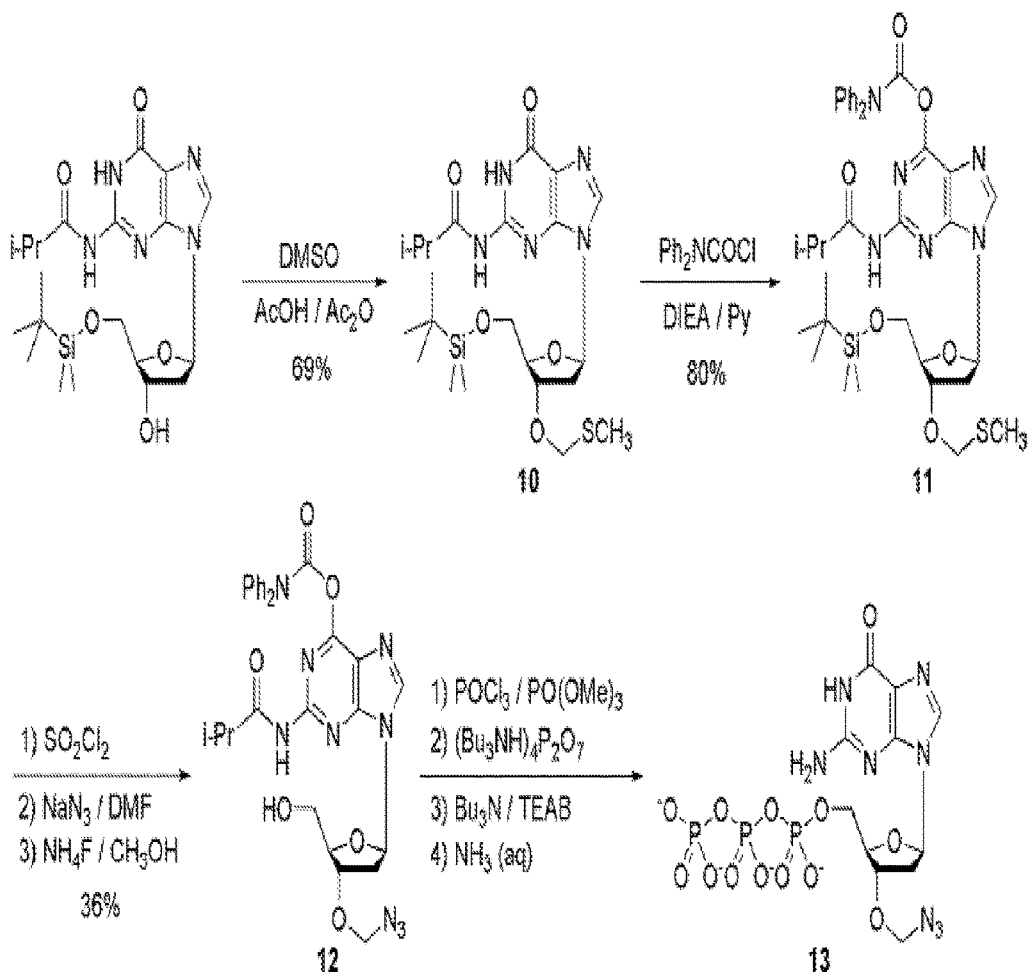
FIG. 10 shows a synthetic scheme for producing 3'-O-azidomethyl deoxyguanosine triphosphate (3'-O-azidomethyl-dGTP).

With reference to FIG. 7, a solution of $N^6$-benzoyl-5'-O-(tert-butyldimethylsilyl)-2'-deoxyadenosine (3.0 g; 6.38 mmol) [CNH Technologies, Woburn, Mass.] in DMSO (12 ml), acetic acid (5.5 ml) and acetic anhydride (17.6 ml) was prepared. The mixture was stirred at room temperature for 48 h. Approximately 100 ml of a saturated $NaHCO_3$ solution was added and the aqueous layer was extracted with $CH_2Cl_2$. The combined organic extract was washed with saturated $NaHCO_3$ solution and dried over $Na_2SO_4$. The residue was purified by flash column chromatography (hexane/ethyl acetate, 1:1 to 1:4) to recover $N^6$-Benzoyl-3'-O-(methylthiomethyl)-5'-O-(tert-butyldimethylsilyl)-2'-deoxyadenosine (shown as compound 1 in FIG. 7) as a white powder (2.4 g; 71% yield). 400 mg of $N^6$-Benzoyl-3'-O-(methylthiomethyl)-5'-O-(tert-butyldimethylsilyl)-2'-deoxyadenosine was dissolved in dry $CH_2Cl_2$ (7 ml) under nitrogen to create a solution (0.76 mmol). Cyclohexene (400 μl), and $SO_2Cl_2$ (155 μl; 1.91 mmol, redistilled) were then added. The reaction mixture was stirred at 0° C. for 2 h. The solvent was then removed under reduced pressure and then under a high-vacuum pump for 10 min. The resulting residue was dissolved in dry DMF (5 ml) and reacted with $NaN_3$ (400 mg; 6.6 mmol) at room temperature for 3 h. The reaction mixture was dispersed in distilled water (50 ml) and extracted with $CH_2Cl_2$. The combined organic layer was dried over $Na_2SO_4$ and concentrated under reduced pressure. The residue was dissolved in MeOH (5 ml) and stirred with $NH_4F$ (300 mg; 8.1 mmol) at room temperature for 24 h. The solvent was then removed under reduced pressure. The reaction mixture was concentrated under reduced pressure and partitioned between water and $CH_2Cl_2$. The organic layer was separated and dried over $Na_2SO_4$. After concentration, the crude product was purified by flash column chromatography (ethyl acetate/methanol) to produce $N^6$-Benzoyl-3'-O-(azidomethyl)-2'-deoxyadenosine (compound 2; FIG. 7) as a white powder (150 mg; 48% yield). $N^6$-Benzoyl-3'-O-(azidomethyl)-2'-deoxyadenosine (123 mg; 0.3 mmol) and a proton sponge (75.8 mg; 0.35 mmol) were then dried in a vacuum desiccator over $P_2O_5$ overnight before dissolving in trimethyl phosphate (600 μl). Next freshly distilled $POCl_3$ (40 μl; 0.35 mmol) was added dropwise at 0° C. and the mixture was stirred at 0° C. for 2 h. Subsequently, a mixture of tributylammonium pyrophosphate (552 mg) and tributylamine (0.55 ml; 2.31 mmol) in anhydrous DMF (2.33 ml) was added at room temperature and stirred for 30 min. Triethyl ammonium bicarbonate solution (TEAB) (0.1 M; pH 8.0; 15 ml) was then added, and the mixture was stirred for 1 hour at room temperature. Subsequently, concentrated $NH_4OH$ (15 ml) was added and stirred overnight at room temperature. The resulting mixture was concentrated under vacuum and the residue was diluted with 5 ml of water. The crude mixture was then purified with anion exchange chromatography on DEAE-Sephadex A-25 at 4° C. using a gradient of TEAB (pH 8.0; 0.1-1.0 M). The crude product was purified with reverse-phase HPLC to produce 3'-O-azidomethyl-dATP (FIG. 7, compound 3), a nucleotide analog to be used for later synthesis.

3'-O-azidomethyl-dTTP

Acetic acid (4.8 ml) and acetic anhydride (15.4 ml) were added to a stirred solution of 5'-O-(tertbutyldimethylsilyl) thymidine (2.0 g; 5.6 mmol) [CNH Technologies, Woburn, Mass.] in DMSO. The reaction mixture was stirred at room temperature for 48 h. A saturated $NaHCO_3$ solution (100 ml) was added, and the aqueous layer was extracted with ethyl acetate (3×100 ml). The combined organic extract was washed with a saturated solution of $NaHCO_3$ and dried over $Na_2SO_4$. After concentration, the crude product was purified by flash column chromatography (hexane/ethyl acetate) to produce 3'-O-(Methylthiomethyl)-5'-O-(tert-butyldimethylsilyl)thymidine (FIG. 8; Compound 4) as a white powder (1.75 g; 75% yield). Approximately 1 gram of 3'-O-(Methylthiomethyl)-5'-O-(tert-butyldimethylsilyl)thymidine was then dissolved in dry $CH_2Cl_2$ (10 ml) under nitrogen. To this mixture cyclohexene (1.33 ml) and $SO_2Cl_2$ (284 µl; 3.5 mmol, redistilled) were added. The resulting mixture was then stirred at 0° C. for 1.5 h. The solvent was then removed under reduced pressure and then under high vacuum for 10 min. The residue was dissolved in dry DMF (5 ml) and reacted with $NaN_3$ (926 mg; 15.4 mmol) at room temperature for 3 h. That reaction mixture was next dispersed in distilled water (50 ml) and extracted with $CH_2Cl_2$ (3×50 ml). The combined organic extract was dried over $Na_2SO_4$ and concentrated under reduced pressure. The residue was dissolved in MeOH (5 ml) and reacted with $NH_4F$ (600 mg; 16.2 mmol) at room temperature for 24 h. The reaction mixture was concentrated under reduced pressure and partitioned between water and $CH_2Cl_2$. The organic layer was then separated and dried over $Na_2SO_4$. After concentration, the residue was purified by flash column chromatography (hexane/ethyl acetate) to produce 3'-O-(azidomethyl)thymidine (FIG. 8, Compound 5) as a white powder (550 mg; 71% yield). Next, the 3'-O-(azidomethyl)thymidine and a proton sponge (0.35 mmol) were dried in a vacuum desiccator over $P_2O_5$ overnight before dissolving in trimethyl phosphate (600 µl). Next, freshly distilled $POCl_3$ (40 µl; 0.35 mmol) was added dropwise at 0° C. and the mixture was stirred at 0° C. for 2 h. Subsequently, a mixture of tributylammonium pyrophosphate (552 mg) and tributylamine (0.55 ml; 2.31 mmol) in anhydrous DMF (2.33 ml) was added at room temperature and stirred for 30 min. Triethyl ammonium bicarbonate solution (TEAB) (0.1 M; pH 8.0; 15 ml) was then added, and the mixture was stirred for 1 hour at room temperature. Subsequently, concentrated $NH_4OH$ (15 ml) was added and stirred overnight at room temperature. The resulting mixture was concentrated under vacuum and the residue was diluted with 5 ml of water. The crude mixture was then purified with anion exchange chromatography on DEAE-Sephadex A-25 at 4° C. using a gradient of TEAB (pH 8.0; 0.1-1.0 M). The crude product was purified with reverse-phase HPLC to produce 3'-O-azidomethyl-dTTP (FIG. 8, compound 6), a nucleotide analog to be used for later synthesis.

3'-O-azidomethyl-dCTP

Three and a half grams of $N^4$-benzoyl-5'-O-(tert-butyldimethylsilyl)-2'-deoxycytidine [CNH Technologies, Woburn, Mass.] was added to 14.7 ml of DMSO to produce a 7.65 mmol solution. To this solution, acetic acid (6.7 ml) and acetic anhydride (21.6 ml) were added, and the reaction mixture was stirred at room temperature for 48 h. A saturated $NaHCO_3$ solution (100 ml) was then added and the aqueous layer was extracted with $CH_2Cl_2$ (3×100 ml). The combined organic extract was washed with a saturated solution of $NaHCO_3$ and then dried over $Na_2SO_4$. After concentration, the crude product was purified by flash column chromatography (ethyl acetate/hexane) to produce $N^4$-Benzoyl-3'-O-(methylthiomethyl)-5'-O-(tert-butyldimethylsilyl)-2'-deoxycytidine (FIG. 9; compound 7) as a white powder (2.9 g; 73% yield). In 8 ml of $CH_2Cl_2$ $N^4$-Benzoyl-3'-O-(methylthiomethyl)-5'-O-(tert-butyldimethylsilyl)-2'-deoxycytidine (558 mg; 1.04 mmol) was dissolved and then cyclohexene (560 µl) and $SO_2Cl_2$ (220 µl; 2.7 mmol) were added. The reaction mixture was stirred at 0° C. for 1 h. The volatiles were then removed with reduced pressure. The remaining residue was dissolved in dry DMF (5 ml) and reacted with $NaN_3$ (400 mg; 6.6 mmol) at room temperature for 2 h. The reaction mixture was dispersed in distilled water (50 ml) and extracted with $CH_2Cl_2$ (3×50 ml). The combined organic extract was dried over $Na_2SO_4$ and concentrated under reduced pressure. The residue was dissolved in MeOH (5 ml) and reacted with $NH_4F$ (600 mg; 16.2 mmol) at room temperature for 24 h. The solvent was removed under reduced pressure. The resulting residue was suspended in water (50 ml) and extracted with $CH_2Cl_2$ (3×50 ml). The combined organic extract was dried over $Na_2SO_4$ and concentrated under reduced pressure. The crude product was purified by flash column chromatography (hexane/ethyl acetate) to produce $N^4$-Benzoyl-3'-O-(azidomethyl)-2'-deoxycytidine (FIG. 9, compound 8) as a white powder (200 mg; 50% yield). Next, the $N^4$-Benzoyl-3'-O-(azidomethyl)-2'-deoxycytidine and a proton sponge (0.35 mmol) were dried in a vacuum desiccator over $P_2O_5$ overnight before dissolving in trimethyl phosphate (600 µl). Then freshly distilled $POCl_3$ (40 µl; 0.35 mmol) was added dropwise at 0° C. and the mixture was stirred at 0° C. for 2 h. Subsequently, a mixture of tributylammonium pyrophosphate (552 mg) and tributylamine (0.55 ml; 2.31 mmol) in anhydrous DMF (2.33 ml) was added at room temperature and stirred for 30 min. Triethyl ammonium bicarbonate solution (TEAB) (0.1 M; pH 8.0; 15 ml) was then added, and the mixture was stirred for 1 hour at room temperature. Subsequently, concentrated $NH_4OH$ (15 ml) was added and stirred overnight at room temperature. The resulting mixture was concentrated under vacuum and the residue was diluted with 5 ml of water. The crude mixture was then purified with anion exchange chromatography on DEAE-Sephadex A-25 at 4° C. using a gradient of TEAB (pH 8.0; 0.1-1.0 M). The crude product was purified with reverse-phase HPLC to produce 3'-O-azidomethyl-dCTP (FIG. 9, compound 9), a nucleotide analog to be used for later synthesis.

3'-O-azidomethyl-dGTP

To a stirred solution of $N^2$-isobutyryl-5'-O-(tert-butyldimethylsilyl)-2'-deoxyguanosine (5 g; 11.0 mmol) [CNH Technologies, Woburn, Mass.] in dry DMSO (21 ml), acetic acid (10 ml) and acetic anhydride (32 ml) were added. The reaction mixture was stirred at room temperature for 48 h. A saturated $NaHCO_3$ solution (100 ml) was added and the aqueous layer was extracted with ethyl acetate (3×100 ml). The combined organic extract was washed with a saturated $NaHCO_3$ solution and dried over $Na_2SO_4$. After concentration, the crude product was purified by flash column chromatography ($CH_2Cl_2$/MeOH) to produce $N^2$-Isobutyryl-3'-O-(methylthiomethyl)-5'-O-(tert-butyldimethylsilyl)-2'-deoxyguanosine (FIG. 10, compound 10) as a white powder (3.9 g; 69% yield). One gram of $N^2$-Isobutyryl-3'-O-(methylthiomethyl)-5'-O-(tert-butyldimethylsilyl)-2'-deoxyguanosine was subsequently added to dry pyridine (22 ml; 2.0 mmol) along with diphenylcarbamoyl chloride (677 mg; 2.92 mmol) and DIEA (N,N-diisopropylethylamine; SIGMA) (1.02 ml; 5.9 mmol). The reaction mixture was stirred under nitrogen atmosphere at room temperature for 3 h. The solvent was removed under high vacuum. The crude product was purified by flash column chromatography (ethyl acetate/hexane) to produce $N^2$-Isobutyryl-$O^6$-(diphenylcarbamoyl)-3'-O-(methylthiomethyl)-5'-O-(tert-butyldimethylsilyl)-2'-deoxyguanosine (FIG. 10, compound 11), which appeared as a yellowish powder (1.09 g; 80% yield). $N^2$—Isobutyryl-$O^6$-(diphenylcarbamoyl)-3'-O-(methylthiomethyl)-5'-O-(tert-butyldimethylsilyl)-2'-deoxyguanosine was then dissolved in dry $CH_2Cl_2$ (1.1 mmol) and stirred under nitrogen atmosphere at 0° C. for 1.5 h. The solvent was removed under reduced pressure and then under high vacuum for 10 min. The resulting residue was dissolved in dry DMF (5 ml) and reacted with $NaN_3$ (600 mg; 10 mmol) at room temperature for 3 h. The reaction mixture was then dispersed in distilled water (50 ml) and extracted with $CH_2Cl_2$ (3×50 ml). The combined organic extract was dried over $Na_2SO_4$ and concentrated under reduced pressure. The resultant residue was dissolved in MeOH (5 ml) and reacted with $NH_4F$ (500 mg; 13.5 mmol) at room temperature for 24 h. The solvent was removed under reduced pressure. The residue was suspended in water (50 ml) and extracted with $CH_2Cl_2$ (3×50 ml). The combined organic extract was dried over $Na_2SO_4$ and concentrated under reduced pressure. The crude product was purified by flash column chromatography (hexane/ethyl acetate) to produce $N^2$-Isobutyryl-$O^6$-(diphenylcarbamoyl)-3'-O-azidomethyl-2'-deoxyguanosine (FIG. 10, compound 12) as a white powder (230 mg; 36% yield). Finally, the $N^2$-Isobutyryl-$O^6$-(diphenylcarbamoyl)-3'-O-azidomethyl-2'-deoxyguanosine and a proton sponge (0.35 mmol) were dried in a vacuum desiccator over $P_2O_5$ overnight before dissolving in trimethyl phosphate (600 µl). Then freshly distilled $POCl_3$ (40 µl; 0.35 mmol) was added dropwise at 0° C. and the mixture was stirred at 0° C. for 2 h. Subsequently, a mixture of tributylammonium pyrophosphate (552 mg) and tributylamine (0.55 ml; 2.31 mmol) in anhydrous DMF (2.33 ml) was added at room temperature and stirred for 30 min. Triethyl ammonium bicarbonate solution (TEAB) (0.1 M; pH 8.0; 15 ml) was then added, and the mixture was stirred for 1 hour at room temperature. Subsequently, concentrated $NH_4OH$ (15 ml) was added and stirred overnight at room temperature. The resulting mixture was concentrated under vacuum and the residue was diluted with 5 ml of water. The crude mixture was then purified with anion exchange chromatography on DEAE-Sephadex A-25 at 4° C. using a gradient of TEAB (pH 8.0; 0.1-1.0 M). The crude product was purified with reverse-phase HPLC to produce 3'-O-azidomethyl-dGTP (FIG. 10, compound 13), a nucleotide analog to be used for later synthesis.

As described with respect to FIG. 2, once a 3'-O-blocked dNTP or 3'-O-blocked rNTP is added, it will be necessary to remove the blocking group so that additional dNTPs or rNTPs can be added. In some embodiments, the 3'-O-blocking group can be removed with a palladium catalyst in neutral aqueous solution at elevated temperature hydrochloric acid to pH 2, a reducing agent such as mercaptoethanol, or by the addition of tris-(2-carboxyethyl)phosphine. See, e.g., U.S. Pat. No. 6,664,079; Meng, et al. *J. Org. Chem.*, 2006, 71(81):3248-52; Bi et al., *J. Amer. Chem. Soc.* 2006; 2542-2543, U.S. Pat. No. 7,279,563, and U.S. Pat. No. 7,414,116, all of which are incorporated herein by reference in their entireties. In other embodiments, the 3'-substitution group may be removed by UV irradiation (see, e.g., WO 92/10587, incorporated by reference herein in its entirety). In some embodiments, the removal of the 3'-O-blocking group does not include chemical cleavage but uses a cleaving enzyme such as alkaline phosphatase.

EXAMPLES

Protein Modifications.

As a starting point for optimizing TdT activity with dNTP analogs with 3'-O-blocking groups, we make 400 ($20^2$) point mutants at Arg336 and/or Arg454 residues to assess the impact on utilization of modified dNTP analogs such as 3'-O-azidomethyl dNTPs as substrates. Protein modifications at these sites act as positive controls for assay development and attempts to increase the activity of TdT with the 3'-O-blocking groups modified dNTP analogs. Subsequently, following these point mutations with saturation mutagenesis of the surrounding regions, we identify sequences that may compensate for the potential reduction in activity due to changes at Arg336 or Arg454, as discussed in the text above.

We also develop 3'-O-azidomethyl-dNTPs as suitable building blocks for enzyme mediated solid support bound oligodeoxynucleotides synthesis by producing and screening a library of ~1000 modified TdT proteins which accept a 3'-O-blocked dNTP as a substrate. In some embodiments, we use PA gel shift assays to screen the modified protein space of hundreds to thousands of TdT sequence variants to verify addition of 3'-O-blocked dNTPs (see Bussow et al., *Genomics*, 2000;65(1):1-8, incorporated herein by reference in its entirety). In other embodiments, we use MALDI-TOF as a high throughput alternative to PA gel shift assays. Automated MALDI-TOF instruments are capable of analyzing hundreds of samples per hour, and can readily detect and differentiate the anticipated mass gain of 304.26-329.27 Da from one of the four nucleotide terminators. MALDI-TOF analysis of oligonucleotides is typically performed in negative-ion mode, to allow for higher sensitivity, higher resolution, and lower fragmentation compared to positive-ion mode. For validation of MALDI-TOF, primer extension is monitored by polyacrylamide (PA) gel shift assays, which are used to quantify the rate of conversion of a n-mer primer to a n+1-mer (see, e.g., Leconte et al., *Angew Chem Int Ed Eng*, 2010; 49(34):5921-24).

Using commercially-available gene synthesis methods (i.e., IDT gBlocks®), we also create single- and double-site mutations at Arg336 and Arg454 to allow for accommodation of 3'-O-blocked dNTPs at the active site of TdT. This minimal library of synthetic TdT genes are inserted into a suitable N-terminal His tagged expression vector, like pRSETA or pET19b (see Kuan et al., *Biochem. Insights*, 2010; 3:41-6, incorporated herein by reference in its entirety), via restriction site or In-Fusion assembly methods (see Sleight et al., *Nucleic Acids Res.*, 2010; 38(8)2624-36, incorporated herein by reference in its entirety). These methods allow us to transform the E. coli host strain DH5a to express the desired proteins. The resulting plasmid library is amplified by DH5a culture in LB media with ampicillin and extracted for subsequent transformation in the E. coli BL21(DE3) expression strain. Each BL21 clone is assigned to one well of a 96-well plate. Sequence identity of the modified TdT gene is verified with standard DNA sequencing. After induction of TdT expression, cells are harvested and lysed. His-tagged TdT are captured from the lysate using a His tag purification resin. The captured protein is eluted from the resin with imidazole and dialyzed into an extension reaction buffer for activity screens.

Computer Modeling.

In order to guide the optimum alteration of a TdT enzyme, we model and design TdT mutant libraries that are used to predict proteins that can bind modified dNTP substrates in a catalytically-productive mode. In particular, we use the Enzyme Design technology within the Rosetta Molecular Modeling Suite (Rosetta Commons, Seattle, Wash.) to model TdT and 3'-O-blocked dNTP analogs. Initially, functional constraints in the form of distance, angles, and dihedrals between the substrate and enzyme are defined in order to enforce a catalytically productive interface during simulations. Design simulations that utilize these functional constraints are then run, during which the combinatorial sequence space of the active site are heuristically sampled, and predicted energies for millions of putative active site sequences are calculated. Additionally, amino acids at the active site interface, with the exception of the catalytic residues, are allowed to change to any of the twenty amino acids; while amino acids outside of the active site interface are kept fixed. At the end of the design run the three-dimensional coordinates of the predicted lowest energy structure are recorded. [As this is a simulated annealing simulation it is generally necessary to run roughly ~1000 design trajectories. Between zero and twenty mutations predicted during a design simulation are generally observed.] The lowest 10% of designs based on energy are selected, and the observed amino acids at each designable position are used to construct a combinatorial library of ~1000 TdT variants. If the 10% cutoff leads to a larger combinatorial space than 1000, a more stringent energy cutoff is used.

After computational selection, the identified TdT genes are subjected to extensive mutagenesis by ordering gBlock fragments with up to 6 amino acid modifications on either side of Arg336 and Arg454 residues. In the case of libraries that require additional sites in the sequence to be modified beyond +/−6 of Arg336 and/or Arg454, additional gBlocks encompassing those regions are used for iterative mutagenesis. Transfected *E. coli* cells are grown in 2 ml 96-well plates, pelleted and lysed in the same plates. Lysate are transferred to 96-well filter plates containing His tag purification resin, washed and eluted from the resin using imidazole.

Eluent containing partially purified recombinant enzyme are dialyzed in-plate into an extension assay reaction buffer for activity screening in 96-well plates. The extension assays are then initiated with the addition of a 20-mer primer and ~1000 uM concentration of each of four 3'-O-azidomethyl-dNTP terminators. After incubation for 12 hrs at 37° C., the reactions are terminated by heating to 70° C. for 10 min. 5 ul of each reaction is transferred to a subsequent 96-well plate and mixed 1:1 with the MALDI-TOF matrix 3-Hydroxypicolinic acid (3-HPA) in acetonitrile with ammonium citrate. 1-2 ul aliquots are spotted onto MALDI plates, dried under vacuum, and subjected to mass analysis of the extension products in negative ion reflector mode on a Bruker Biflex IV MALDI-TOF MS (Bruker Corp., Billerica, Mass.). Screening takes ~1 hour per MALDI plate enabling a search of a large amount of modified protein space. MALDI-MS analysis is used to detect the molecular weight gain (304.26-329.27) due to the addition of a single nucleotide terminator. To increase sensitivity, MALDI matrices are varied by using 2,3,4-Trihydroxyacetophene (2,3,4-THAP) in acetonitrile with ammonium citrate, or α-Cyano-4-hydroxycinnamic acid (CHCA) in acetonitrile and trifluoroacetic acid. ZipTips with C18 resin may also be used to desalt and concentrate the oligonucleotide product. An oligonucleotide standard is used for reference during instrument calibration.

De Novo Synthesis.

Once screening is completed, the engineered TdT developed above and two different 3'-O—R reversible terminator dNTP analogs (i.e., dATP & dCTP), are used in a prototype process using an initiator attached to a solid support with the manual addition of extension reaction reagents and wash buffers. 5'-biotin-dT10 is immobilized on commercially available streptavidin (SA)-coated magnetic beads and used as a support-bound oligonucleotide initiator using standard protocols. The 3'-O—R reversible terminator dNTP analogs, e.g., 3'-O-azidomethyl-dNTP analogs, are used at high concentrations (approx. 1 mM) to insure quantitative TdT-mediated incorporations in 1-5 min reaction times. After removal of the unreacted dNTPs with extensive washing, the 3'-O—R reversible terminator is removed. For example, 3'-O-azidomethyl block groups are removed by treatment with 0.5M TCEP (pH 10) at 60° C. for 5'. After several rounds of enzymatic incorporation of the nucleotide analogs, the resulting oligonucleotide are analyzed via MALDI-TOF. [Previous studies have shown that biotinylated substrates immobilized on magnetic streptavidin beads can be analyzed directly by MALDI-TOF, without removal from the bead surface (see Zhou, *Anal Biochem,* 2011; 408:5-11, incorporated by reference herein in its entirety).] The resulting analysis is used to estimate the completeness of utilization of the initiating primers, homopolymer formation due to failure of the terminating species, and the extent of n−1 formation indicative of failure to extend, or failure to deblock the 3'—OR group to completion.

After proof of principle with a limited set of 3'-O—R reversible terminator dNTP analogs, complete de novo oligonucleotide synthesis will be achieved with the newly engineered enzymes by using repeated bind-wash-unblock steps as described in FIG. 2 and the accompanying text.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:

1. A modified terminal deoxynucleotidyl transferase (TdT) comprising a mutation in the TGSR motif and capable of adding a nucleotide analog comprising a removable 3'-O-blocking moiety to the 3'-OH of a nucleic acid initiator in the absence of a nucleic acid template.

2. The modified TdT of claim 1, wherein the modified TdT comprises an N-terminus t-138 bovine TdT and a protein tag sequence fused to the N-terminus.

3. The modified TdT of claim 1, wherein the modified TdT comprises an N-terminus t-151 bovine TdT and a protein tag sequence fused to the N-terminus.

4. The modified TdT of claim 1, wherein the modified TdT comprises an N-terminus t-160 bovine TdT and a protein tag sequence fused to the N-terminus.

5. The modified TdT of claim 1, wherein the modified TdT exhibits an increased rate of incorporation of modified nucleotides, compared to native TdT.

6. The modified TdT of claim 1, wherein the modified TdT is capable of adding adenine, cytosine, guanine, and thymine deoxyribonucleotides modified with a removable 3'-O-blocking moiety.

7. The modified TdT of claim 6, wherein said nucleotides are 2'-deoxyribonucleotides.

8. The modified TdT of claim 1, wherein the modified TdT is capable of adding adenine, cytosine, guanine, and uracil ribonucleotides modified with a removable 3'-O-blocking moiety.

9. The modified TdT of claim 1, wherein said removable 3'-O-blocking moiety comprises a 3'-O-azidomethyl group.

10. The modified TdT of claim 1, wherein said removable 3'-O-blocking moiety comprises a 3'-O-amino group.

11. The modified TdT of claim 1, wherein said removable 3'-O-blocking moiety comprises a 3'-O-allyl group.

12. The modified TdT of claim 1, wherein said removable 3'-O-blocking moiety is selected from the group consisting of O-phenoxyacetyl; O-methoxyacetyl; O-acetyl; O-(p-toluene)sulfonate; O-phosphate; O-nitrate; O-[4-methoxy]-tetrahydrothiopyranyl; O-tetrahydrothiopyranyl; O-[5-methyl]-tetrahydrofuranyl; O-[2-methyl,4-methoxy]-tetrahydropyranyl; O-[5-methyl]-tetrahydropyranyl; and O-tetrahydrothiofuranyl.

13. The modified TdT of claim 1, wherein the modified TdT is capable of incorporating a 3'-O-blocked nucleotide 5'-triphosphate, and said removable blocking moiety comprises a group selected from esters, ethers, carbonitriles, phosphates, carbonates, carbamates, hydroxylamine, borates, nitrates, sugars, phosphoramide, phosphoramidates, phenylsulfenates, sulfates, sulfones and amino acids.

14. The modified TdT of claim 1, wherein the modified TdT is capable of incorporating modified nucleotides at a reaction temperature of about 30° C.

15. The modified TdT of claim 1, wherein the modified TdT is capable of incorporating modified nucleotides at a reaction temperature from 30° C. to 80° C.

16. The modified TdT of claim 1, wherein the modified TdT is capable of incorporating modified nucleotides at a concentration of 1000 μM or less.

17. The modified TdT of claim 16, wherein the modified TdT is capable of incorporating modified nucleotides at a concentration of 100 μM or less.

18. The modified TdT of claim 1, wherein the modified TdT is expressed by an organism having a genome comprising a nucleic acid sequence being at least 90% identical to SEQ ID NOS: 2, 4, 6, or 8.

19. The modified TdT of claim 1, wherein the TGSR motif comprises a mutation selected from G, A, V, L, I, M, F, W, P, S, T, C, Y, N, Q, D, E, K, R, or H.

* * * * *

SEQUENCE LISTING

```
<160> NUMBER OF SEQ ID NOS: 9

<210> SEQ ID NO 1
<211> LENGTH: 520
<212> TYPE: PRT
<213> ORGANISM: Bos taurus

<400> SEQUENCE: 1
```

-continued

```
Met Ala Gln Gln Arg Gln His Gln Arg Leu Pro Met Asp Pro Leu Cys
1               5                   10                  15

Thr Ala Ser Ser Gly Pro Arg Lys Arg Pro Arg Gln Val Gly Ala
            20                  25                  30

Ser Met Ala Ser Pro Pro His Asp Ile Lys Phe Gln Asn Leu Val Leu
        35                  40                  45

Phe Ile Leu Glu Lys Lys Met Gly Thr Thr Arg Arg Asn Phe Leu Met
50                  55                  60

Glu Leu Ala Arg Arg Lys Gly Phe Arg Val Glu Asn Glu Leu Ser Asp
65                  70                  75                  80

Ser Val Thr His Ile Val Ala Glu Asn Asn Ser Gly Ser Glu Val Leu
                85                  90                  95

Glu Trp Leu Gln Val Gln Asn Ile Arg Ala Ser Ser Gln Leu Glu Leu
            100                 105                 110

Leu Asp Val Ser Trp Leu Ile Glu Ser Met Gly Ala Gly Lys Pro Val
            115                 120                 125

Glu Ile Thr Gly Lys His Gln Leu Val Val Arg Thr Asp Tyr Ser Ala
            130                 135                 140

Thr Pro Asn Pro Gly Phe Gln Lys Thr Pro Pro Leu Ala Val Lys Lys
145                 150                 155                 160

Ile Ser Gln Tyr Ala Cys Gln Arg Lys Thr Thr Leu Asn Asn Tyr Asn
                165                 170                 175

His Ile Phe Thr Asp Ala Phe Glu Ile Leu Ala Glu Asn Ser Glu Phe
            180                 185                 190

Lys Glu Asn Glu Val Ser Tyr Val Thr Phe Met Arg Ala Ala Ser Val
            195                 200                 205

Leu Lys Ser Leu Pro Phe Thr Ile Ile Ser Met Lys Asp Thr Glu Gly
            210                 215                 220

Ile Pro Cys Leu Gly Asp Lys Val Lys Cys Ile Ile Glu Glu Ile Ile
225                 230                 235                 240

Glu Asp Gly Glu Ser Ser Glu Val Lys Ala Val Leu Asn Asp Glu Arg
                245                 250                 255

Tyr Gln Ser Phe Lys Leu Phe Thr Ser Val Phe Gly Val Gly Leu Lys
            260                 265                 270

Thr Ser Glu Lys Trp Phe Arg Met Gly Phe Arg Ser Leu Ser Lys Ile
            275                 280                 285

Met Ser Asp Lys Thr Leu Lys Phe Thr Lys Met Gln Lys Ala Gly Phe
290                 295                 300

Leu Tyr Tyr Glu Asp Leu Val Ser Cys Val Thr Arg Ala Glu Ala Glu
305                 310                 315                 320

Ala Val Gly Val Leu Val Lys Glu Ala Val Trp Ala Phe Leu Pro Asp
                325                 330                 335

Ala Phe Val Thr Met Thr Gly Gly Phe Arg Arg Gly Lys Lys Ile Gly
            340                 345                 350

His Asp Val Asp Phe Leu Ile Thr Ser Pro Gly Ser Ala Glu Asp Glu
            355                 360                 365

Glu Gln Leu Leu Pro Lys Val Ile Asn Leu Trp Glu Lys Lys Gly Leu
            370                 375                 380

Leu Leu Tyr Tyr Asp Leu Val Glu Ser Thr Phe Glu Lys Phe Lys Leu
385                 390                 395                 400

Pro Ser Arg Gln Val Asp Thr Leu Asp His Phe Gln Lys Cys Phe Leu
                405                 410                 415
```

```
Ile Leu Lys Leu His His Gln Arg Val Asp Ser Ser Lys Ser Asn Gln
            420                 425                 430

Gln Glu Gly Lys Thr Trp Lys Ala Ile Arg Val Asp Leu Val Met Cys
            435                 440                 445

Pro Tyr Glu Asn Arg Ala Phe Ala Leu Leu Gly Trp Thr Gly Ser Arg
        450                 455                 460

Gln Phe Glu Arg Asp Ile Arg Arg Tyr Ala Thr His Glu Arg Lys Met
465                 470                 475                 480

Met Leu Asp Asn His Ala Leu Tyr Asp Lys Thr Lys Arg Val Phe Leu
                485                 490                 495

Lys Ala Glu Ser Glu Glu Ile Phe Ala His Leu Gly Leu Asp Tyr
            500                 505                 510

Ile Glu Pro Trp Glu Arg Asn Ala
            515                 520

<210> SEQ ID NO 2
<211> LENGTH: 1923
<212> TYPE: DNA
<213> ORGANISM: Bos taurus

<400> SEQUENCE: 2
ctcttctgga gataccactt gatggcacag cagaggcagc atcagcgtct tcccatggat      60
ccgctgtgca cagcctcctc aggccctcgg aagaagagac ccaggcaggt gggtgcctca     120
atggcctccc ctcctcatga catcaagttt caaaatttgg tcctcttcat tttggagaag     180
aaaatgggaa ccacccgcag aaacttcctc atggagctgg ctcgaaggaa aggtttcagg     240
gttgaaaatg agctcagtga ttctgtcacc cacattgtag cagaaaacaa ctctggttca     300
gaggttctcg agtggcttca ggtacagaac ataagagcca gctcgcagct agaactcctt     360
gatgtctcct ggctgatcga agtatgggga gcaggaaaac cagtggagat tacaggaaaa     420
caccagcttg ttgtgagaac agactattca gctaccccaa acccaggctt ccagaagact     480
ccaccacttg ctgtaaaaaa gatctcccag tacgcgtgtc aaagaaaaac cactttgaac     540
aactataacc acatattcac ggatgccttt gagatactgg ctgaaaattc tgagtttaaa     600
gaaaatgaag tctcttatgt gacatttatg agagcagctt ctgtacttaa atctctgcca     660
ttcacaatca tcagtatgaa ggatacagaa ggaattccct gcctggggga caaggtgaag     720
tgtatcatag aggaaattat tgaagatgga gaaagttctg aagttaaagc tgtgttaaat     780
gatgaacgat atcagtcctt caaactcttt acttctgttt ttggagtggg actgaagaca     840
tctgagaaat ggttcaggat gggggttcaga tctctgagta aaataatgtc agacaaaacc     900
ctgaaattca caaaaatgca gaaagcagga tttctctatt atgaagacct tgtcagctgc     960
gtgaccaggg ccgaagcaga ggcggttggc gtgctggtta agaggctgtg tgggcatt     1020 ctgccggatg cctttgtcac catgacagga ggattccgca ggggtaagaa gattgggcat    1080
gatgtagatt ttttaattac cagcccagga tcagcagagg atgaagagca acttttgcct    1140
aaagtgataa acttatggga aaaaagggga ttacttttat attatgacct tgtggagtca    1200
acatttgaaa agttcaagtt gccaagcagg caggtggata ctttagatca ttttcaaaaa    1260
tgctttctga ttttaaaatt gcaccatcag agagtagaca gtagcaagtc caaccagcag    1320
gaaggaaaga cctggaaggc catccgtgtg gacctggtta tgtgccccta cgagaaccgt    1380
gcctttgccc tgctaggctg gactggctcc cggcagtttg agagagacat ccggcgctat    1440
gccacacacg agcggaagat gatgctggat aaccacgctt tatatgacaa gaccaagagg    1500
```

-continued

```
gtatttctca aagcggaaag tgaagaagaa atctttgcac atctgggatt ggactacatt     1560
gaaccatggg aaagaaatgc ttaggagaaa gctgtcaact tttttctttt ctgttctttt     1620
tttcaggtta gacaaattat gcttcatatt ataatgaaag atgccttagt caagtttggg     1680
attctttaca ttttaccaag atgtagattg cttctagaaa taagtagttt tggaaacgtg     1740
atcaggcacc ccctgggtta tgctctggca agccatttgc aggactgatg tgtagaactc     1800
gcaatgcatt ttccatagaa acagtgttgg aattggtggc tcatttccag ggaagttcat     1860
caaagcccac tttgcccaca gtgtagctga aatactgtat acttgccaat aaaaatagga     1920
aac                                                                    1923
```

```
<210> SEQ ID NO 3
<211> LENGTH: 392
<212> TYPE: PRT
<213> ORGANISM: Bos taurus

<400> SEQUENCE: 3
```

```
Met Arg Gly Ser His His His His His His Arg Thr Asp Tyr Ser Ala
1               5                   10                  15

Thr Pro Asn Pro Gly Phe Gln Lys Thr Pro Leu Ala Val Lys Lys
            20                  25                  30

Ile Ser Gln Tyr Ala Cys Gln Arg Lys Thr Thr Leu Asn Asn Tyr Asn
        35                  40                  45

His Ile Asp Ala Phe Glu Ile Leu Ala Glu Asn Ser Glu Phe Lys Glu
    50                  55                  60

Asn Glu Val Ser Tyr Val Thr Phe Met Arg Ala Ala Ser Val Leu Lys
65                  70                  75                  80

Ser Leu Pro Phe Thr Ile Ile Ser Met Lys Asp Thr Phe Thr Glu Gly
                85                  90                  95

Ile Pro Cys Leu Gly Asp Lys Val Lys Cys Ile Ile Glu Glu Ile Ile
            100                 105                 110

Glu Asp Gly Glu Ser Ser Glu Val Lys Ala Val Leu Asn Asp Glu Arg
        115                 120                 125

Tyr Gln Ser Phe Lys Leu Ser Val Phe Gly Val Gly Leu Lys Thr Ser
    130                 135                 140

Glu Lys Trp Phe Arg Met Gly Phe Thr Phe Arg Ser Leu Ser Lys Ile
145                 150                 155                 160

Met Ser Asp Lys Thr Leu Lys Lys Met Gln Lys Ala Gly Phe Leu Tyr
                165                 170                 175

Tyr Glu Asp Leu Val Ser Cys Val Thr Arg Ala Glu Ala Glu Ala Val
            180                 185                 190

Gly Val Leu Val Lys Glu Ala Val Trp Ala Phe Leu Pro Asp Ala Phe
        195                 200                 205

Val Thr Met Thr Gly Gly Phe Arg Arg Gly Lys Lys Ile Gly His Asp
    210                 215                 220

Val Asp Phe Leu Ile Thr Ser Pro Gly Ser Ala Glu Asp Glu Glu Gln
225                 230                 235                 240

Leu Leu Pro Lys Val Ile Asn Leu Trp Glu Lys Lys Gly Leu Leu Leu
                245                 250                 255

Tyr Tyr Asp Leu Val Glu Ser Thr Phe Glu Lys Phe Lys Phe Thr Leu
            260                 265                 270

Pro Ser Arg Gln Val Asp Thr Leu Asp His Phe Gln Lys Cys Phe Leu
        275                 280                 285

Ile Leu Lys Leu His His Gln Arg Val Asp Ser Ser Lys Ser Asn Gln
```

```
Gln Glu Gly Lys Thr Trp Lys Ala Ile Arg Val Asp Leu Val Met Cys
305                 310                 315                 320

Pro Tyr Glu Asn Arg Ala Phe Ala Leu Leu Gly Trp Thr Gly Ser Arg
                325                 330                 335

Gln Phe Glu Arg Asp Ile Arg Arg Tyr Ala Thr His Glu Arg Lys Met
            340                 345                 350

Met Leu Asp Asn His Ala Leu Tyr Asp Lys Thr Lys Arg Val Phe Leu
        355                 360                 365

Lys Ala Glu Ser Glu Glu Ile Phe Ala His Leu Gly Leu Asp Tyr
    370                 375                 380

Ile Glu Pro Trp Glu Arg Asn Ala
385                 390
```

<210> SEQ ID NO 4
<211> LENGTH: 1187
<212> TYPE: DNA
<213> ORGANISM: Bos taurus

<400> SEQUENCE: 4

| | | | | | |
|---|---|---|---|---|---|
| atgagaggat | cgcatcacca | tcaccatcac | agaacagact | attcagctac | cccaaaccca | 60 |
| ggcttccaga | agactccacc | acttgctgta | aaaagatct | cccagtacgc | gtgtcaaaga | 120 |
| aaaaccactt | tgaacaacta | taaccacata | ttcacggatg | cctttgagat | actggctgaa | 180 |
| aattctgagt | ttaaagaaaa | tgaagtctct | tatgtgacat | ttatgagagc | agcttctgta | 240 |
| cttaaatctc | tgccattcac | aatcatcagt | atgaaggata | cagaaggaat | tccctgcctg | 300 |
| ggggacaagg | tgaagtgtat | catagaggaa | attattgaag | atggagaaag | ttctgaagtt | 360 |
| aaagctgtgt | taaatgatga | acgatatcag | tccttcaaac | tctttacttc | tgtttttgga | 420 |
| gtgggactga | agacatctga | gaatggttc | aggatggggt | tcagatctct | gagtaaaata | 480 |
| atgtcagaca | aaaccctgaa | attcacaaaa | atgcagaaag | caggatttct | ctattatgaa | 540 |
| gaccttgtca | gctgcgtgac | cagggccgaa | gcagaggcgg | ttggcgtgct | ggttaaagag | 600 |
| gctgtgtggg | catttctgcc | ggatgccttt | gtcaccatga | caggaggatt | ccgcaggggt | 660 |
| aagaagattg | gcatgatgt | agattttta | attaccagcc | aggatcagc | agaggatgaa | 720 |
| gagcaacttt | tgcctaaagt | gataaactta | tgggaaaaaa | agggattact | tttatattat | 780 |
| gaccttgtgg | agtcaacatt | tgaaaagttc | aagttgccaa | gcaggcaggt | ggatacttta | 840 |
| gatcattttc | aaaaatgctt | tctgatttta | aaattgcacc | atcagagagt | agacagtagc | 900 |
| aagtccaacc | agcaggaagg | aaagacctgg | aaggccatcc | gtgtggacct | ggttatgtgc | 960 |
| ccctacgaga | accgtgcctt | tgccctgcta | ggctggactg | ctcccggca | gtttgagaga | 1020 |
| gacatccggc | gctatgccac | acacgagcgg | aagatgatgc | tggataacca | cgctttatat | 1080 |
| gacaagacca | agagggtatt | tctcaaagcg | gaaagtgaag | aagaaatctt | tgcacatctg | 1140 |
| ggattggact | acattgaacc | atgggaaaga | aatgcttaag | cttgcgc | | 1187 |

<210> SEQ ID NO 5
<211> LENGTH: 379
<212> TYPE: PRT
<213> ORGANISM: Bos taurus

<400> SEQUENCE: 5

```
Met Arg Gly Ser His His His His His His Lys Thr Pro Pro Leu Ala
1               5                   10                  15
```

```
Val Lys Lys Ile Ser Gln Tyr Ala Cys Gln Arg Lys Thr Thr Leu Asn
                 20                  25                  30

Asn Tyr Asn His Ile Asp Ala Phe Glu Ile Leu Ala Glu Asn Ser Glu
             35                  40                  45

Phe Lys Glu Asn Glu Val Ser Tyr Val Thr Phe Met Arg Ala Ala Ser
         50                  55                  60

Val Leu Lys Ser Leu Pro Phe Thr Ile Ile Ser Met Lys Asp Thr Phe
 65                  70                  75                  80

Thr Glu Gly Ile Pro Cys Leu Gly Asp Lys Val Lys Cys Ile Ile Glu
                 85                  90                  95

Glu Ile Ile Glu Asp Gly Glu Ser Ser Glu Val Lys Ala Val Leu Asn
                100                 105                 110

Asp Glu Arg Tyr Gln Ser Phe Lys Leu Ser Val Phe Gly Val Gly Leu
            115                 120                 125

Lys Thr Ser Glu Lys Trp Phe Arg Met Gly Phe Thr Phe Arg Ser Leu
130                 135                 140

Ser Lys Ile Met Ser Asp Lys Thr Leu Lys Met Gln Lys Ala Gly
145                 150                 155                 160

Phe Leu Tyr Tyr Glu Asp Leu Val Ser Cys Val Thr Arg Ala Glu Ala
                165                 170                 175

Glu Ala Val Gly Val Leu Val Lys Glu Ala Val Trp Ala Phe Leu Pro
                180                 185                 190

Asp Ala Phe Val Thr Met Thr Gly Gly Phe Arg Arg Gly Lys Lys Ile
            195                 200                 205

Gly His Asp Val Asp Phe Leu Ile Thr Ser Pro Gly Ser Ala Glu Asp
210                 215                 220

Glu Glu Gln Leu Leu Pro Lys Val Ile Asn Leu Trp Glu Lys Lys Gly
225                 230                 235                 240

Leu Leu Leu Tyr Tyr Asp Leu Val Glu Ser Thr Phe Glu Lys Phe Lys
                245                 250                 255

Phe Thr Leu Pro Ser Arg Gln Val Asp Thr Leu Asp His Phe Gln Lys
            260                 265                 270

Cys Phe Leu Ile Leu Lys Leu His His Gln Arg Val Asp Ser Ser Lys
        275                 280                 285

Ser Asn Gln Gln Glu Gly Lys Thr Trp Lys Ala Ile Arg Val Asp Leu
290                 295                 300

Val Met Cys Pro Tyr Glu Asn Arg Ala Phe Ala Leu Leu Gly Trp Thr
305                 310                 315                 320

Gly Ser Arg Gln Phe Glu Arg Asp Ile Arg Tyr Ala Thr His Glu
                325                 330                 335

Arg Lys Met Met Leu Asp Asn His Ala Leu Tyr Asp Lys Thr Lys Arg
            340                 345                 350

Val Phe Leu Lys Ala Glu Ser Glu Glu Ile Phe Ala His Leu Gly
            355                 360                 365

Leu Asp Tyr Ile Glu Pro Trp Glu Arg Asn Ala
370                 375

<210> SEQ ID NO 6
<211> LENGTH: 1148
<212> TYPE: DNA
<213> ORGANISM: Bos taurus

<400> SEQUENCE: 6
atgagaggat cgcatcacca tcaccatcac aagactccac cacttgctgt aaaaaagatc    60
```

```
tcccagtacg cgtgtcaaag aaaaaccact ttgaacaact ataaccacat attcacggat    120
gcctttgaga tactggctga aaattctgag tttaaagaaa atgaagtctc ttatgtgaca    180
tttatgagag cagcttctgt acttaaatct ctgccattca caatcatcag tatgaaggat    240
acagaaggaa ttccctgcct gggggacaag gtgaagtgta tcatagagga aattattgaa    300
gatggagaaa gttctgaagt taaagctgtg ttaaatgatg aacgatatca gtccttcaaa    360
ctctttactt ctgttttttgg agtgggactg aagacatctg agaaatggtt caggatgggg    420
ttcagatctc tgagtaaaat aatgtcagac aaaaccctga aattcacaaa atgcagaaa     480 gcaggatttc tctattatga agaccttgtc agctgcgtga ccagggccga agcagaggcg    540
gttggcgtgc tggttaaaga ggctgtgtgg gcatttctgc cggatgcctt tgtcaccatg    600
acaggaggat tccgcagggg taagaagatt gggcatgatg tagattttt aattaccagc     660 ccaggatcag cagaggatga agagcaactt ttgcctaaag tgataaactt atgggaaaaa    720
aagggattac ttttatatta tgaccttgtg gagtcaacat ttgaaaagtt caagttgcca    780
agcaggcagg tggatacttt agatcatttt caaaaatgct ttctgatttt aaaattgcac    840
catcagagag tagacagtag caagtccaac cagcaggaag gaaagacctg gaaggccatc    900
cgtgtggacc tggttatgtg ccccctacgag aaccgtgcct ttgccctgct aggctggact    960
ggctcccggc agtttgagag agacatccgg cgctatgcca cacacgagcg gaagatgatg   1020
ctggataacc acgctttata tgacaagacc aagagggtat tctcaaagc ggaaagtgaa    1080 gaagaaatct ttgcacatct gggattggac tacattgaac catgggaaag aaatgcttaa   1140
gcttgcgc                                                           1148

<210> SEQ ID NO 7
<211> LENGTH: 370
<212> TYPE: PRT
<213> ORGANISM: Bos taurus

<400> SEQUENCE: 7

Met Arg Gly Ser His His His His His His Ile Ser Gln Tyr Ala Cys
1               5                   10                  15

Gln Arg Lys Thr Thr Leu Asn Asn Tyr Asn His Ile Asp Ala Phe Glu
                20                  25                  30

Ile Leu Ala Glu Asn Ser Glu Phe Lys Glu Asn Glu Val Ser Tyr Val
            35                  40                  45

Thr Phe Met Arg Ala Ala Ser Val Leu Lys Ser Leu Pro Phe Thr Ile
        50                  55                  60

Ile Ser Met Lys Asp Thr Phe Thr Glu Gly Ile Pro Cys Leu Gly Asp
65                  70                  75                  80

Lys Val Lys Cys Ile Ile Glu Glu Ile Ile Glu Asp Gly Glu Ser Ser
                85                  90                  95

Glu Val Lys Ala Val Leu Asn Asp Glu Arg Tyr Gln Ser Phe Lys Leu
            100                 105                 110

Ser Val Phe Gly Val Gly Leu Lys Thr Ser Glu Lys Trp Phe Arg Met
        115                 120                 125

Gly Phe Thr Phe Arg Ser Leu Ser Lys Ile Met Ser Asp Lys Thr Leu
    130                 135                 140

Lys Lys Met Gln Lys Ala Gly Phe Leu Tyr Tyr Glu Asp Leu Val Ser
145                 150                 155                 160

Cys Val Thr Arg Ala Glu Ala Glu Ala Val Gly Val Leu Val Lys Glu
                165                 170                 175
```

```
Ala Val Trp Ala Phe Leu Pro Asp Ala Phe Val Thr Met Thr Gly Gly
            180                 185                 190

Phe Arg Arg Gly Lys Lys Ile Gly His Asp Val Asp Phe Leu Ile Thr
        195                 200                 205

Ser Pro Gly Ser Ala Glu Asp Glu Glu Gln Leu Leu Pro Lys Val Ile
    210                 215                 220

Asn Leu Trp Glu Lys Lys Gly Leu Leu Leu Tyr Tyr Asp Leu Val Glu
225                 230                 235                 240

Ser Thr Phe Glu Lys Phe Lys Phe Thr Leu Pro Ser Arg Gln Val Asp
                245                 250                 255

Thr Leu Asp His Phe Gln Lys Cys Phe Leu Ile Leu Lys Leu His His
            260                 265                 270

Gln Arg Val Asp Ser Ser Lys Ser Asn Gln Gln Glu Gly Lys Thr Trp
        275                 280                 285

Lys Ala Ile Arg Val Asp Leu Val Met Cys Pro Tyr Glu Asn Arg Ala
    290                 295                 300

Phe Ala Leu Leu Gly Trp Thr Gly Ser Arg Gln Phe Glu Arg Asp Ile
305                 310                 315                 320

Arg Arg Tyr Ala Thr His Glu Arg Lys Met Met Leu Asp Asn His Ala
                325                 330                 335

Leu Tyr Asp Lys Thr Lys Arg Val Phe Leu Lys Ala Glu Ser Glu Glu
            340                 345                 350

Glu Ile Phe Ala His Leu Gly Leu Asp Tyr Ile Glu Pro Trp Glu Arg
        355                 360                 365

Asn Ala
    370

<210> SEQ ID NO 8
<211> LENGTH: 1121
<212> TYPE: DNA
<213> ORGANISM: Bos taurus

<400> SEQUENCE: 8
atgagaggat cgcatcacca tcaccatcac atctcccagt acgcgtgtca agaaaaaacc    60
actttgaaca actataacca catattcacg gatgcctttg atactggc tgaaaattct     120 gagtttaaag aaaatgaagt ctcttatgtg acatttatga gagcagcttc tgtacttaaa   180
tctctgccat tcacaatcat cagtatgaag gatacagaag gaattccctg cctgggggac   240
aaggtgaagt gtatcataga ggaaattatt gaagatggag aaagttctga gttaaagct    300 gtgttaaatg atgaacgata tcagtccttc aaactcttta cttctgtttt tggagtggga   360
ctgaagacat ctgagaaatg gttcaggatg gggttcagat ctctgagtaa aataatgtca   420
gacaaaaccc tgaaattcac aaaaatgcag aaagcaggat ttctctatta tgaagacctt   480
gtcagctgcg tgaccagggc cgaagcagag gcggttggcg tgctggttaa agaggctgtg   540
tgggcatttc tgccggatgc ctttgtcacc atgacaggag gattccgcag ggtaagaag    600 attgggcatg atgtagattt tttaattacc agcccaggat cagcagagga tgaagagcaa   660 ctttttgccta aagtgataaa cttatgggaa aaaaagggat actttttata ttatgacctt   720
gtggagtcaa catttgaaaa gttcaagttg ccaagcaggc aggtggatac tttagatcat   780
tttcaaaaat gctttctgat tttaaaattg caccatcaga gagtagacag tagcaagtcc   840
aaccagcagg aaggaaagac ctggaaggcc atccgtgtgg acctggttat gtgcccctac   900
gagaaccgtg cctttgccct gctaggctgg actggctccc ggcagtttga gagagacatc   960
```

-continued

```
cggcgctatg ccacacacga gcggaagatg atgctggata accacgcttt atatgacaag    1020
accaagaggg tatttctcaa agcggaaagt gaagaagaaa tctttgcaca tctgggattg    1080
gactacattg aaccatggga agaaatgct taagcttgcg c                         1121
```

<210> SEQ ID NO 9
<211> LENGTH: 510
<212> TYPE: PRT
<213> ORGANISM: Mus musculus

<400> SEQUENCE: 9

```
Met Asp Pro Leu Gln Ala Val His Leu Gly Pro Arg Lys Lys Arg Pro
1               5                   10                  15

Arg Gln Leu Gly Thr Pro Val Ala Ser Thr Pro Tyr Asp Ile Arg Phe
            20                  25                  30

Arg Asp Leu Val Leu Phe Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Leu Gln Asn Ile Lys Ala Ser
                85                  90                  95

Ser Glu Leu Glu Leu Leu Asp Ile Ser Trp Leu Ile Glu Cys Met Gly
            100                 105                 110

Ala Gly Lys Pro Val Glu Met Met Gly Arg His Gln Leu Val Val Asn
        115                 120                 125

Arg Asn Ser Ser Pro Ser Pro Val Pro Gly Ser Gln Asn Val Pro Ala
    130                 135                 140

Pro Ala Val Lys Lys Ile Ser Gln Tyr Ala Cys Gln Arg Arg Thr Thr
145                 150                 155                 160

Leu Asn Asn Tyr Asn Gln Leu Phe Thr Asp Ala Leu Asp Ile Leu Ala
                165                 170                 175

Glu Asn Asp Glu Leu Arg Glu Asn Glu Gly Ser Cys Leu Ala Phe Met
            180                 185                 190

Arg Ala Ser Ser Val Leu Lys Ser Leu Pro Phe Pro Ile Thr Ser Met
        195                 200                 205

Lys Asp Thr Glu Gly Ile Pro Cys Leu Gly Asp Lys Val Lys Ser Ile
    210                 215                 220

Ile Glu Gly Ile Ile Glu Asp Gly Glu Ser Ser Glu Ala Lys Ala Val
225                 230                 235                 240

Leu Asn Asp Glu Arg Tyr Lys Ser Phe Lys Leu Phe Thr Ser Val Phe
                245                 250                 255

Gly Val Gly Leu Lys Thr Ala Glu Lys Trp Phe Arg Met Gly Phe Arg
            260                 265                 270

Thr Leu Ser Lys Ile Gln Ser Asp Lys Ser Leu Arg Phe Thr Gln Met
        275                 280                 285

Gln Lys Ala Gly Phe Leu Tyr Tyr Glu Asp Leu Val Ser Cys Val Asn
    290                 295                 300

Arg Pro Glu Ala Glu Ala Val Ser Met Leu Val Lys Glu Ala Val Val
305                 310                 315                 320

Thr Phe Leu Pro Asp Ala Leu Val Thr Met Thr Gly Gly Phe Arg Arg
                325                 330                 335

Gly Lys Met Thr Gly His Asp Val Asp Phe Leu Ile Thr Ser Pro Glu
            340                 345                 350
```

```
Ala Thr Glu Asp Glu Glu Gln Gln Leu Leu His Lys Val Thr Asp Phe
        355             360             365
Trp Lys Gln Gln Gly Leu Leu Leu Tyr Cys Asp Ile Leu Glu Ser Thr
    370             375             380
Phe Glu Lys Phe Lys Gln Pro Ser Arg Lys Val Asp Ala Leu Asp His
385             390             395             400
Phe Gln Lys Cys Phe Leu Ile Leu Lys Leu Asp His Gly Arg Val His
                405             410             415
Ser Glu Lys Ser Gly Gln Gln Glu Gly Lys Gly Trp Lys Ala Ile Arg
                420             425             430
Val Asp Leu Val Met Cys Pro Tyr Asp Arg Arg Ala Phe Ala Leu Leu
        435             440             445
Gly Trp Thr Gly Ser Arg Gln Phe Glu Arg Asp Leu Arg Arg Tyr Ala
    450             455             460
Thr His Glu Arg Lys Met Met Leu Asp Asn His Ala Leu Tyr Asp Arg
465             470             475             480
Thr Lys Arg Val Phe Leu Glu Ala Glu Ser Glu Glu Ile Phe Ala
                485             490             495
His Leu Gly Leu Asp Tyr Ile Glu Pro Trp Glu Arg Asn Ala
            500             505             510
```